(12) United States Patent
Kutsaev et al.

(10) Patent No.: US 11,540,382 B2
(45) Date of Patent: Dec. 27, 2022

(54) COMPACT HIGH GRADIENT ION ACCELERATING STRUCTURE

(71) Applicant: RADIABEAM TECHNOLOGIES, LLC, Santa Monica, CA (US)

(72) Inventors: Sergey Kutsaev, Santa Monica, CA (US); Ronald Agustsson, Venice, CA (US); Alexander Smirnov, Santa Monica, CA (US)

(73) Assignee: RadiaBeam Technologies, LLC, Santa Monica, CA (US)

( * ) Notice: Subject to any disclaimer, the term of this patent is extended or adjusted under 35 U.S.C. 154(b) by 339 days.

(21) Appl. No.: 16/669,215

(22) Filed: Oct. 30, 2019

(65) Prior Publication Data
US 2020/0068699 A1    Feb. 27, 2020

Related U.S. Application Data

(63) Continuation of application No. PCT/US2018/030980, filed on May 3, 2018.
(Continued)

(51) Int. Cl.
H05H 7/12 (2006.01)
H05H 7/00 (2006.01)
H05H 9/04 (2006.01)

(52) U.S. Cl.
CPC ............. H05H 7/12 (2013.01); H05H 7/001 (2013.01); H05H 9/045 (2013.01); H05H 2007/122 (2013.01)

(58) Field of Classification Search
CPC .......... H05H 7/12; H05H 7/001; H05H 9/045; H05H 2007/122; H05H 9/00; H05H 9/044; A61N 5/1077; A61N 2005/1087
(Continued)

(56) References Cited

U.S. PATENT DOCUMENTS 2,945,981 A * 7/1960 Karp ................... H01J 25/46
313/156
5,578,909 A * 11/1996 Billen ................. H05H 9/00
315/505
(Continued)

FOREIGN PATENT DOCUMENTS

CA    2790793    1/2011
EP    2516006    3/2014

OTHER PUBLICATIONS

Ostroumov et al., "Compact Carbon Ion LINAC", Proceeding of NA-PAC2016 Chicago, IL, Oct. 14, 2016, pp. 1-3 (Year: 2016).*
(Continued)

*Primary Examiner* — Alexander H Taningco
*Assistant Examiner* — Amy X Yang
(74) *Attorney, Agent, or Firm* — Knobbe, Martens, Olson & Bear, LLP

(57) ABSTRACT

A high gradient linear accelerating structure can propagate high frequency waves at a negative harmonic to accelerate low-energy ions. The linear accelerating structure can provide a gradient of 50 MV/m for particles at a $\beta$ of between 0.3 and 0.4. The high gradient structure can be a part of a linear accelerator configured to provide an energy range from an ion source to 450 MeV/u for $^{12}C^{6+}$ and 250 MeV for protons. The linear accelerator can include one or more of the following sections: a radiofrequency quadrupole (RFQ) accelerator operating at the sub-harmonic of the S-band frequency, a high gradient structure for the energy range from ~45 MeV/u to ~450 MeV/u.

16 Claims, 21 Drawing Sheets

Related U.S. Application Data

(60) Provisional application No. 62/502,405, filed on May 5, 2017.

(58) Field of Classification Search
USPC ........................................................ 315/500
See application file for complete search history.

(56) References Cited

U.S. PATENT DOCUMENTS

| | | | | |
|---|---|---|---|---|
| 6,376,990 | B1* | 4/2002 | Allen | H05H 9/04 |
| | | | | 315/505 |
| 6,465,957 | B1* | 10/2002 | Whitham | H05H 9/04 |
| | | | | 378/65 |
| 6,646,383 | B2* | 11/2003 | Bertsche | H05H 7/22 |
| | | | | 315/505 |
| 7,046,765 | B2 | 5/2006 | Wong et al. | |
| 7,411,361 | B2 | 8/2008 | Agustsson et al. | |
| 7,423,381 | B2* | 9/2008 | Hanna | H05H 7/18 |
| | | | | 315/505 |
| 7,764,324 | B2 | 7/2010 | Andonian et al. | |
| 8,148,922 | B2 | 4/2012 | Cleland et al. | |
| 8,947,115 | B2 | 2/2015 | Rosenzweig et al. | |
| 9,023,765 | B1 | 5/2015 | Rimmer et al. | |
| 9,847,205 | B2 | 12/2017 | Sherman et al. | |
| 9,913,360 | B1 | 3/2018 | Antipov et al. | |
| 10,212,800 | B2 | 2/2019 | Agustsson et al. | |
| 2011/0290379 | A1 | 12/2011 | Murokh et al. | |
| 2013/0163707 | A1 | 1/2013 | Habs et al. | |
| 2015/0057484 | A1* | 2/2015 | Amaldi | A61N 5/1067 |
| | | | | 600/1 |
| 2015/0338545 | A1 | 11/2015 | Arodzero et al. | |
| 2018/0343733 | A1* | 11/2018 | Mustapha | H05H 7/04 |
| 2019/0320523 | A1 | 10/2019 | Agustsson et al. | |

OTHER PUBLICATIONS

Ostroumov et al., "Compact Carbon Ion Linac," Argonne National Laboratory NAPAC-2016, pp. 1-23 (Year: 2016).*
Benedetti et al., High Gradient Linac for Proton Therapy, Physical Review Accelerators and Beams 20 120401, Apr. 13, 2017.
Cowley, Cyberknife 6D Robotic Radiosurgery Presentation, stored on Mar. 17, 2017.
Kutsaev, et al., A dual-energy linac cargo inspection system, Instruments and Experimental Techniques, 2011, vol. 54, No. 2, pp. 241-248.
Kutsaev, A New Thermionic RF Electtron Gun for Synchrotron Light Sources, in 4 pages.
Kutsaev, Beam Dynamics Studies for A Compact Carbon Ion Linac for Therapy, pp. 947-949.
Kutsaev, Sergey V., High Gradient S-band Accelerating Structure for Hadron Therapy Linac*, Jun. 7, 2016, Radiabeam Systems, pp. 1-23.
Kutsaev, Hellweg2D code for design of high average power traveling wave linacs, Accelerator Seminar at SLAC National Accelerator Laboratory, Sep. 1, 2016 in 28 pages.
Kutsaev, et al. High Gradient Accelerating Structures for Carbon Therapy Linac, in 4 pages.
Kutsaev, et al., Accelerating Structure for C-Band Electron Linear Accelerator Optimization, Proceedings of LINAC08, Victoria, BC, Canada, pp. 922-924.
Kutsaev, et al., Beam optics Studies fora uranium ion micro beam, Oct. 2014, in 6 pages.
Kutsaev, et al., Compact 4kW Variable RF Power Coupler for FRIB Quarter-Wave Cavities, in 3 pages.
Kutsaev, et al., Compact Electron Linear Accelerator Relus-5 for Radiation Technology Application, Proceedings of EPAC 2006, Edinburgh, Scotland, in 3 pages.
Kutsaev, et al. , Electron Accelerators for Novel Cargo Inspection Methods, ScienceDirect, Physics Procedia 90 (2017) 115-125.
Kutsaev, et al., High Gradient Superconducting Cavity Development for FFAG, Sep. 2013, in 3 pages.
Kutsaev, et al., High Power RF Coupler for ADS Accelerating Cavities, Proceedings of SRF2013, Paris France, pp. 1050-1052.
Kutsaev, et al., High-gradient low-accelerating structure using the first negative spatial harmonic of the fundamental mode, Physical Review Special Topics—Accelerators and Beams, Dec. 2007, in 17 pages.
Kutsaev, t al., Hybrid Electron Linac Based on Magnetic Coupled Accelerating Structure, Applications of Accelerators, Tech Transfer, Industry Accel/Storage Rings 08: Linear Accelerators, pp. 2136-2138.
Kutsaev, et al., Improved charge breeding efficiency of light ions with an electron cyclotron resonance ion source AIP Review of Scientific Instruments 83, 2012 American Institute of Physics.
Kutsaev, et al., Input Couplers for the Dipole Mode Periodic Structures, Proceedings of RuPAC-2010, Protvino, Russia, pp. 328-331.
Kutsaev, et al., Magnetic Coupled Disk-Loaded Waveguide, Proceedings of RuPAC-2010, Protvino, Russia, pp. 319-321.
Kutsaev, et al.,Multifactor Simulations in Axisymmetric and Non-Axisymmetric Radio Frequency Structures, Proceedings of RuPAC 2008, Zvenigarad, Russia, pp. 215-217.
Kutsaev, et al. , Single-Shot THZ Spectrometer For Bunch Length Measurements, Logicware, Inc. New York, in 3 pages.
Kutsaev, et al., Upgrade of Argonne's CW SC Heavy Ion Accelerator, Proceedings of PAC2013, Pasadena, CA, pp. 737-739.
Kutsaev, et al., High Gradient S-Band Accelerating Structure for Hadron Therapy Linac, Jun. 7, 2016, in 23 pages.
Kutsaev, Single-shot mm-wave spectrometer for RF breakdown detection in linear accelerators, Jun. 8, 2016, in 22 pages.
Kutsaev, Sergey V., et al. Electron Linac with Deep Energy Control for Adaptive Rail Cargo Inspection System. This work has been partially supported by the US Department of Homeland Security, Domestic Nuclear Detection Office, under competitively awarded contract/IAA HSHQDC-13-C-B0019.
Smirnov, A.V., et al. Multi-cell disk-and-ring tapered structure for compact RF linacs, Nuclear Instruments and Methods in Physics Research A 830, 2016, pp. 294-302.
International Search Report—PCT/US2018/023881 filed Mar. 22, 2018, dated Aug. 9, 2018, 11 pages.
International Search Report—PCT/US2018/030980 filed May 3, 2018, dated Aug. 2, 2018, 6 pages.
International Search Report—PCT/US2018/035346 filed May 31, 2018, dated Sep. 6, 2018, 7 pages.

* cited by examiner

COMPACT HIGH GRADIENT ION ACCELERATING STRUCTURE

CROSS-REFERENCE TO RELATED APPLICATIONS

This application claims the benefit of priority under 35 U.S.C. § 111(a) to International Application No. PCT/US2018/030980, filed on May 3, 2018, entitled "COMPACT HIGH GRADIENT ION ACCELERATING STRUCTURE," and claims the benefit of priority under 35 U.S.C. § 119(e) to U.S. Provisional Application No. 62/502,405, filed May 5, 2017, entitled "COMPACT HIGH GRADIENT ION ACCELERATING STRUCTURE," each of which is hereby incorporated by reference herein in its entirety and for all purposes.

STATEMENT REGARDING FEDERALLY SPONSORED R&D

This invention was funded, in part, by government support under DOE Grant No. DE-SC0015717. The government has certain rights in the invention.

BACKGROUND

Field

The present disclosure relates to radiation therapy, in particular to beam generation and beam hardware.

SUMMARY

Modern radiation therapy techniques tend to rely on bulky machinery with a limited scope of volumetric angles at which therapy can be administered.

Systems and methods disclosed herein address various challenges related to particle therapy and particle acceleration.

Described herein are various embodiments of linear accelerators ("linacs") and related components. A linac is a device commonly used for external beam radiation generation and may be used in medical treatments. As will become clear from the following disclosure, producing an effective high-gradient linac structure can present a variety of technical challenges, which may be solved by many of the novel features disclosed herein.

In some embodiments, a high-gradient accelerating structure can be configured to accelerate particles. The structure can include a plurality of accelerating cells. Each of the plurality of accelerating cells can include an iris. The iris of each of the plurality of accelerating cells can include an aperture that is coaxial with a beam axis. The aperture can be configured to allow a beam of particles to pass therethrough. The iris can include a nose that has a maximum thickness greater than an iris thickness. The high gradient accelerating structure can be configured to receive the beam of particles along the beam axis at a beam velocity and to propagate electromagnetic waves at a negative first harmonic synchronous with the beam of particles.

In some embodiments, the high-gradient accelerating structure has a total length of less than 45 m. The high-gradient accelerating structure may be configured to accelerate the beam of particles at speeds greater than 0.3 times the speed of light.

In some embodiments, a high-gradient accelerating structure can be configured to accelerate particles. The high gradient accelerating structure can include a plurality of high gradient tanks that are arranged along a beam axis. The structure can include a negative harmonic structure (NHS) tank. The NHS tank can include a plurality of accelerating cells. Each of the plurality of accelerating cells can include an iris. The iris of each of the plurality of accelerating cells can include an aperture that is coaxial with the beam axis and a nose that is disposed radially about the aperture. The nose can have a maximum thickness greater than an iris thickness. The high gradient accelerating structure can be configured to propagate electromagnetic waves at a negative harmonic synchronous with particles having a beam velocity greater than 0.3 times the speed of light.

In some embodiments, a cell component for use in a linear particle accelerator can include a body that defines a cell cavity. The cell component can include an iris. The iris may include a central aperture that is configured to be disposed about a beam axis of the linear particle accelerator. The iris can include a plurality of holes that are disposed circumferentially around the aperture. The iris can further include a nose that is disposed radially between the aperture and the plurality of holes. The nose may have a thickness that is greater than a thickness of the iris.

In some embodiments, a first radial portion of the nose includes an increasing thickness radially from the beam axis and a second radial portion includes a decreasing thickness radially from the beam axis. The cell component may be configured to receive a beam of particles along the beam axis and to propagate electromagnetic waves at a negative harmonic synchronous with the beam of particles.

BRIEF DESCRIPTION OF THE DRAWINGS

Certain embodiments of the present disclosure will now be described, by way of example only, with reference to the accompanying drawings. From figure to figure, the same or similar reference numerals are used to designate similar components of an illustrated embodiment.

DETAILED DESCRIPTION

Figure 1A:
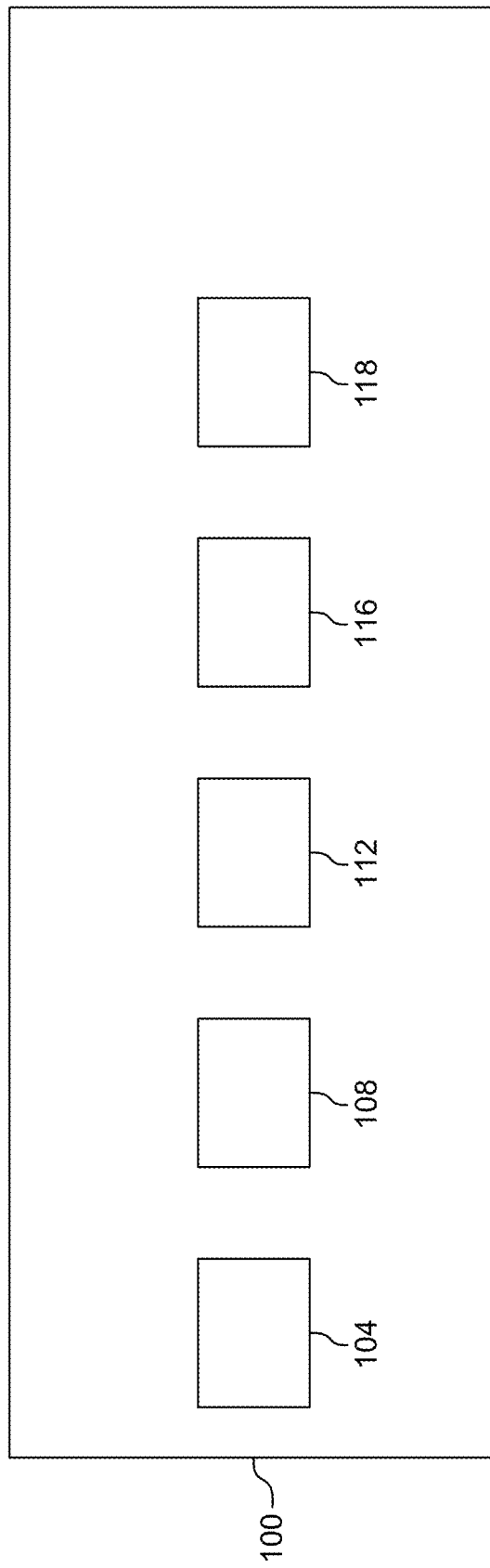
FIG. 1A shows a schematic of an example linear accelerator that includes one or more elements.

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Linear accelerator: a device for accelerating particles such as subatomic particles and/or ions where particles pass through each cell only once.

Cell element (or sometimes "cell"): a component of a linear accelerator that may include a cell body and a cell iris. Cell elements may be individually manufactured.

High gradient: applying an energy gain gradient of greater than about 30 MV/m to particles, or other similar values that may vary based on frequency.

Accelerating cell: a cell through which particles are accelerated.

Particles: subatomic or atomic elements, such as hadrons, that can be accelerated in a linear accelerator.

Phase velocity: rate at which the phase of an electromagnetic wave propagates. The velocity may be positive or negative.

S-band frequency: portion of the electromagnetic spectrum spanning roughly between 2 GHz and 4 GHz.

Beam velocity: average rate at which particles within a beam of particles are traveling over a small distance.

Radiation therapy is the branch of medicine that deals with the treatment of cancer by delivering high-energy beams directly to a tumor or another intended target. Carbon therapy is one of the most promising among techniques for cancer treatment. Cyclotrons and synchrotrons are currently used for this purpose but are expensive and bulky constructions with large magnets, have significant problems with rapid and efficient energy adjustment, and cannot provide an effective acceleration of the different species of ions within the same design. A linear accelerator (or "linac") is a promising alternative to cyclic machines, although their use is limited by the requirement to develop novel high gradient accelerating structures to enable this technology. To achieve a footprint of 40 m in a carbon linac, 35 MV/m real-estate or at least 50 MV/m accelerating gradients may be used.

A high-gradient linear accelerator may be used for the delivery of ion beams with end-energies up to 450 MeV/u for $^{12}C^{6+}$ ions and 250 MeV for protons. To achieve its compactness, an accelerating structure capable of providing 50 MV/m for the particles with beta equal to 0.3 may be used. Such high accelerating gradients can use, for example, a range of waves within the S-band frequency. For some S-band structures with low betas, some limitations may arise when either the surface fields are too high or the shunt impedance is too low. A cavity containing a beam that is synchronous with a higher spatial harmonic may be used.

Radiation therapy is a large segment of clinical oncology, where treatment can be administered by delivering ionizing radiation beams directly to the tumor. Existing radiation therapy machines can use beams of X-rays or hadrons (e.g., protons or other positive ions) for treatment, and although about 60% of all cancer patients undergo some form of radiotherapy, only about 1% of all radiotherapy patients receive treatment by high energy particles. Hadron therapy may improve localization of the dose to the tumor volume and spare healthy tissues relative to traditional X-ray therapy. This may be due to the characteristic "Bragg peak" depth-dose distribution in tissues. In some estimates as much as 15% of patients can benefit from the hadron therapy options.

Radiation treatments using both proton and carbon beams can be costly and can prevent hadron therapy from becoming the standard of care for a wider range of cancers. A usable device for cancer therapy may need to produce up to 200-250 MeV protons or/and up to 400-450 MeV/u carbon ions. Both cyclotrons and synchrotrons that may be used for this purpose can be expensive and bulky constructions with large magnets, and they may have significant problems with rapid and/or efficient energy adjustment. Proton therapy centers can cost more than $100 million, and carbon therapy centers can be twice as expensive or more. In comparison, a standard photon therapy linac can cost about $3 million, and even with civil construction costs, a brand new conventional radiotherapy clinic may cost less than $10 million.

Within hadron therapy, proton therapy may be the most common, although studies indicate that the carbon ion therapy may offer additional advantages, and a proton and carbon therapy combined could achieve an even more precise dose confinement to the tumor volume, while sparing healthy tissues. A system that can provide both proton and carbon beams is highly desirable. This cannot be achieved by some designs of cyclotrons and synchrotrons.

An ultra-high gradient linear accelerator can provide a more full energy range from a particle (e.g., ion) source to 450 MeV/u for $^{12}C^{6+}$ and 250 MeV for protons, which can include one or more of the following sections: a radiofrequency quadrupole (RFQ) accelerator operating at the sub-harmonic of the S-band frequency, a high gradient structure for the energy range from about 45 MeV/u to about 450 MeV/u. The structure can be configured to operate at the $-1^{st}$ harmonic and may be capable of producing a 50 MV/m gradient at peak field levels of about 20% lower than some modern linacs and thus lower RF breakdown rate. The high gradient structure can be configured to handle a beam of particles (e.g., ions) that have a ratio of charge to mass of between about 0.4 to 1.

Some designs may offer various features. For example, the high gradient structure (HGS) described herein may provide accelerating gradients of up to 50 MV/m for particles with β=0.3, which exceeds gradients of 3-5 MV/m for such low-beta structures. The symbol β (or "beta") represents a ratio of a velocity to the speed of light. In some embodiments, a negative harmonic may be used to allow use of one or more noses near the aperture of corresponding cells (e.g., on the cell iris). This may increase the power efficiency of the structure by 50% or more compared to other structures. As a further example, the structure may include an optimized elliptical shape of the noses to allow keeping the peak electric fields below an RF break down reliability limit (e.g., of 160 MV/m). Magnetic coupling holes in the disk-loaded structure can be used to allow keeping the gradient at the 50 MV/m level along a greater portion (e.g., the whole length) of the multi-cell structure without reducing the aperture radius. The designed structure of some embodiments can be scalable and/or used for lower- and/or higher-beta ions.

The embodiments of HGS described herein (e.g., the high gradient structure 118 described below) can be configured to operate on various hadrons (e.g., $p^+$ and $^{12}C^{6+}$) and operate on a relative beam velocity (β) of as low as 0.3. An operating frequency can be less than 3000 MHz and in some embodiments below 2900 MHz. For example, in some embodiments the operating frequency is about 2997 MHz. In some embodiments the operating frequency of the HGS is about 2856 MHz. The HGS can be configured to propagate a backwards traveling wave (BTW), though other designs such as forward traveling wave (FTW) structures, biperiodic structures (BPS), side-coupled structures (SCL), and/or disk-and-washer (DAW) structures may be possible. The HGS can be configured to operate on a non-fundamental harmonic (e.g., negative first ($-1^{st}$)).

The HGS can be configured to provide an accelerating gradient of greater than about 20 MV/m, greater than about 30 MV/m, greater than about 40 MV/m, and preferably at least about 50 MV/m or greater. In some embodiments, the HGS can be configured to achieve a shunt impedance (MΩ/m) of greater than about 20 MΩ/m, and preferably greater than about 30 MΩ/m, such as 32 MΩ/m. In some embodiments, the HGS can be configured to have a peak electric field less than about 200 MV/m, preferably less than about 180 MV/m, and most preferably equal to or less than about 160 MV/m. The HGS can be configured to achieve a Poynting vector of less than 2.5 MW/mm², preferably less than about 1.5 MW/mm², and may be about 1.3 MW/mm².

An accelerating gradient of 50 MV/m may be used to facilitate a linac footprint of no more than about 40 m. Such high accelerating gradients may be obtained at high frequency (e.g., 2856 MHz), a low duty cycle (e.g., <0.06%), and/or very short beam pulses (e.g., <0.5 μs).

RF breakdown limits exist for various linac designs. For example, peak surface fields of 250 MV/m at 11-12 GHz and about 160 MV/m for S-band may exist in RF guns and/or side-coupled linacs. Peak surface magnetic fields can cause pulse heating, which may damage the structure if the peak temperature rise is higher than a threshold temperature (e.g., 50° C.). A unified criterion, such as a modified Poynting vector (<S>) may impact the gradients as well. A predicted limit for some structures may be about 2.8 MW/mm². Accordingly, a Poynting vector below this value may be preferred. For a design having a 50 MV/m, β=0.3 structure, it may be advantageous to keep one or more of these parameters below these limits.

A π-mode coupled cavity linac (CCL) structure may be used for high-gradient structures because of its low peak field to accelerating gradient ratio. Although CCL-type accelerating structures demonstrate excellent performance when designed for particles with high β, its RF parameters may degrade dramatically for structures with β<0.7. Also, when designing the multi-cell structure, it may be helpful to take into account the neighbor mode separation, which may be the minimum for a π-mode. For a 28.5-cm π-mode section, 18 cells may be used, which can result in sub-MHz mode separation. This can present challenges to tuning and locking into a π-mode regime. Developing a standing wave (SW) structure, operating in π/2-mode and/or switching to the traveling wave (TW) operation regime may address some of these challenges. In some embodiments it may not be desirable to use a SW option for β=0.43 structure and/or for β=0.3.

For TW structures, such as the disk-loaded structure, to compensate the field attenuation due to the power losses, the iris diameter can be reduced along the waveguide. In some designs, a coupling can be provided by magnetic fields via coupling holes in the iris. This may allow for increasing a coupling coefficient, which may leave the aperture radius substantially constant. In some instances, this may not reduce the shunt impedance of the cell. The magnetic coupling can make the dispersion negative, so the phase and group velocities may have different signs, and the wave can travels from the output coupler towards the input coupler. This can be referred to as a backward travelling wave (BTW) regime. In some embodiments, a 50 MV/m, β=0.4, 2856-MHz, 5π/6 magnetically coupled structure section can be used (see, e.g., FIG. 2C).

The design peak electric field for β=0.4 may be 219 MV/m, which may be above a reliable 160-MV/m RFBD limit. These peak field values may be located at the nose tips of the structure (see FIG. 2C). By reducing the phase velocity to β=0.3, the cell length $$L = \frac{\beta\lambda\theta}{2\pi}$$

and the distance between noses can become 25% shorter, which may increase a peak electric field. In some such cases, it may be desirable to bring the fields down to 160 MV/m levels, as described in further detail herein. To do so, the noses may be removed from the cell geometry. This may reduce the concentration of the electric field near the aperture and/or reduce the shunt impedance by about 40% as calculated for the case of β=0.43.

A novel cavity can be implemented where the beam is synchronous not with the fundamental spatial harmonic, for example, but with the higher harmonic. Periodic structures have an infinite number of spatial harmonics. These harmonics may have the same frequency but different spatial field distribution. An accelerating structure can be designed for the m=−1 harmonic which can make the accelerating period longer. In structures with longer periods, noses may be implemented to increase the shunt impedance without a significant increase in the peak fields.

The scope of RF design and optimization of the accelerating cell can include the choice of the optimal phase advance per cell, the optimization of the coupling holes and noses, and/or the preliminary structural stability considerations. It may be advantageous to maximize the shunt impedance of the structure while keeping the peak electric fields below 160 MV/m, the pulsed heating gradient below 50K, and/or the modified Poynting vector module below 2.8 MW/mm².

The shunt impedance of a fundamental harmonic BTW cell with fixed aperture radius of 3 mm, a coupling hole diameter of 8 mm, and an iris thickness of 1.5 mm can be affected by the phase advance. For example, the highest shunt impedance may be achieved for $\theta=2\pi/3$. These parameters can be used as a reference for comparison with those of the negative-harmonic structure.

For structures where the beam is synchronous with the spatial harmonic of the order m, the accelerating cell length may be calculated as $$L = \frac{\beta_m \lambda |\theta + 2\pi m|}{2\pi}.$$

For m=−1, $$L = \frac{\beta \lambda (2\pi - \theta)}{2\pi},$$

the cell is $$\frac{2\pi}{\theta} - 1$$

times longer than the one operating at fundamental harmonic. Some embodiments may include a 20-cell model with periodic boundary conditions with the structure cell length optimized for the first negative harmonic with the phase advance of $2\pi/3$ and $\beta=0.3$ (L=2/3·0.3·λ). For a beam that is not synchronous with any harmonics, the voltage gain may be zero. The beam may be synchronous with the fundamental harmonic (e.g., for β=0.6), the first negative harmonic (m=−1, β=0.3), and the first positive harmonic (m=+1, e.g., for β=0.15) (see, e.g., FIG. 13), which demonstrates acceleration of the particles in the structure operating at the higher harmonics.

The amplitudes of higher harmonics reduce dramatically (see FIG. 13), so the resulting shunt impedance of a $2\pi/3$ fundamental harmonic structure (FHS) may be ~1.5 times higher than the shunt impedance of a $2\pi/3$ first negative harmonic structure (NHS). To compensate the reduced energy gain due to the smaller amplitude, noses described herein in the NHS may be introduced. This can concentrate the electric field near the beam axis and/or improve the shunt impedance. The most proximal tanks (relative to the particle source) of the high gradient structure 118 may include NHS tanks. The NHS tanks may be configured to accelerate a beam of particles at beam velocities of β of 0.3, 0.32, 0.35, 0.37, 0.4, or any range or value within those values. The total number of NHS tanks may include fewer than about five tanks and preferably about two tanks. Other tanks may be distal the NHS tanks. For example, some tanks that are distal the NHS tanks may include backward traveling wave (BTW) tanks. Additionally or alternatively, other tanks, such as forward traveling wave (FTW) tanks may be included distal the NHS tanks. The BTW tanks may be configured to accelerate a beam of particles at beam velocities of β greater than or equal to about 0.4, 0.45, 0.5, 0.55, 0.60, 0.65, 0.70, 0.75, 0.80, 0.85, 0.90, 0.95, or 1, for example, or any range or value within those values.

The nose may have an elliptical profile. This may minimize the surface electric field on it. The nose profile can be formed by a cylindrical surface and/or by the intersection of an ellipse with a cone. Magnetic coupling between cells can be performed with a plurality of holes in the iris with uniform angular spacing. The number of holes may be between 2 and 24 holes and in some embodiments is 16 or 8. An accelerating gap, the nose ellipse profile, and the angle may be optimized to obtain the highest shunt impedance while targeting the ratio of peak electric field to the accelerating gradient $E_{max}/E_{acc}$ to be ≤3.2, which corresponds to 160 MV/m maximum surface electric field. In negative harmonic BTW, the maximum shunt impedance and lower peak electric field can be achieved for the phase advances close to π. Since the group velocity of the π-mode may be zero, some embodiments may be operated at 5π/6 mode.

Turning now to the Figures, various embodiments of high gradient structures, linacs, other structures, and methods will now be disclosed. FIG. 1A shows a schematic of an example linear accelerator 100 that includes one or more elements. As shown, a linear accelerator 100 can include a particle source 104, a pre-accelerator 108, a drift tube linac section 112, a coupled drift tube linac section 116, and/or a high gradient structure 118. One or more of these elements 104, 108, 112, 116 may be disposed along a beam path. In some embodiments, the beam path includes a beam axis along which each element 104, 108, 112, 116, 118 is disposed.

Figure 1B:
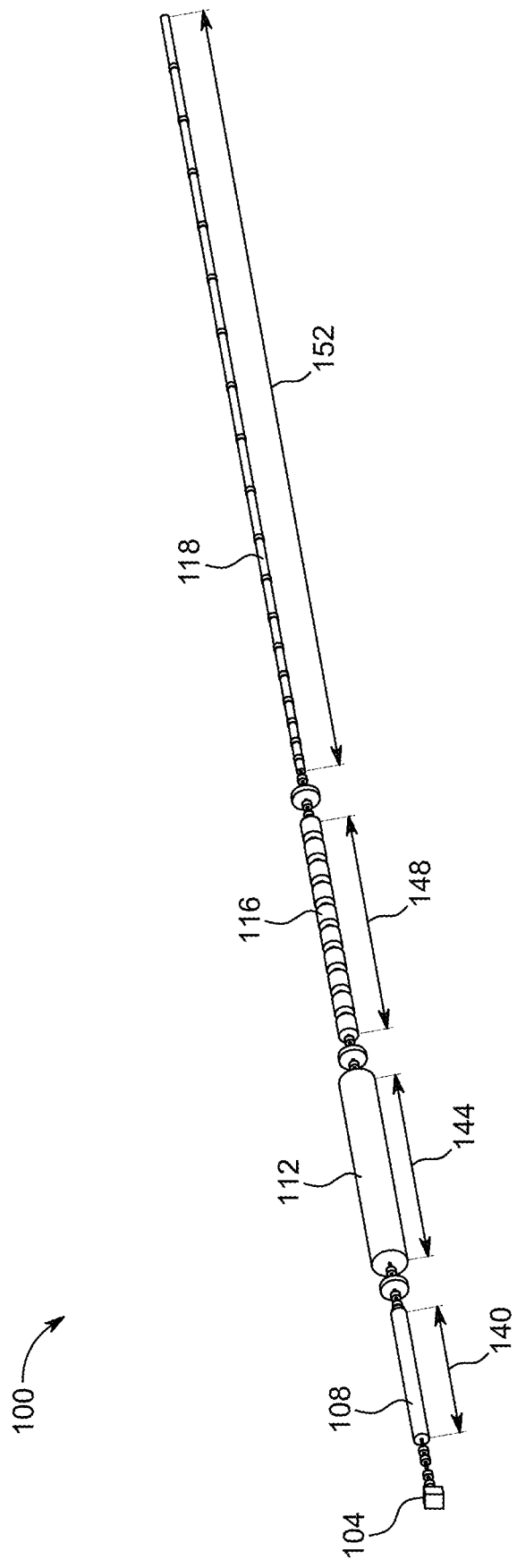
FIG. 1B shows an example configuration of a linear accelerator of FIG. 1A.

FIG. 1B shows an example configuration of a linear accelerator 100 of FIG. 1A. The particle source 104 can be any source of hadron (e.g., ions such as protons or carbon ions) or other particle. For example, protons and/or carbon ions (e.g., $^{12}C^{5+}$) may be used. Certain charges of ions may be preferable. For example, a 5+ charge state may be preferred to reduce mixture of the ions with other species (e.g., oxygen ions). The particle source 104 can be located at a first end of the linear accelerator 100. The particle source 104 may be configured to emit a beam of particles into the pre-accelerator 108. The particle source 104 can be configured to emit radiation doses of between about 300 million carbon ions per second and 1 billion carbon ions per second. In some embodiments, the particle source 104 is configured to emit between about 5 billion protons per second and 15 billion protons per second. In some designs, the particle source 104 is configured to emit about 10 billion protons per second. The particle source 104 may operate on a pulse current of between about 1 and 100 μA, and in some embodiments the pulse current may be between about 27 μA. The beam of ions may be separated into between about 0.1 μs and 10 μs pulses. For example, in some embodiments the pulses may be about 0.5 μs. The particle source 104 can be a modern electron cyclotron resonance (ECR) ion source. The particle source 104, in combination with other elements, may achieve a beam pulse width of between about 0.5 μs and 10 μs and may be about 1 μs. The filling time may be between about 0.1 and 3 μs and may be about 0.5 μs. The repetition rate may be between about 1 Hz and 400 Hz and in some embodiments is about 120 Hz.

The linear accelerator 100 may have a relatively short length. This can provide improved portability of the location of the structure. The system can have the ability to provide a high gradient accelerating structure with a limited footprint and improved overall efficiency of the linear device. In some designs, the system can achieve a 50 MV/m accelerating gradient in the final element of the linac (e.g., the high gradient structure 118), to reach 450 MeV/u carbon ions acceleration, while maintaining the length of the entire linear accelerator 100 below 50 m. The linear accelerator 100 may have a length of between 40 m and 50 m. In some embodiments the length of the linear accelerator 100 is between about 35 m and 47 m. The length may be about 45 m in some embodiments.

The pre-accelerator 108 can have bunching and/or focusing properties. The pre-accelerator 108 may include a radiofrequency quadrupole (RFQ) accelerator or some other accelerator. The pre-accelerator 108 can be configured to accelerate the particles emitted by the particle source 104 to between about 1 MeV/u to 5 MeV/u. For example, in some embodiments the pre-accelerator 108 can accelerate emitted particles to up to about 3 MeV/u. The operating frequency of the pre-accelerator 108 can be between about 60 MHz and 960 MHz. In some embodiments, the operating frequency is about 476 MHz. This can provide effective beam acceptance into the higher-frequency sections of the linear accelerator 100. The pre-accelerator 108 may include a foil configured to convert certain ions into others (e.g., $^{12}C^{5+}$ to $^{12}C^{6+}$). The length 140 of the pre-accelerator 108 can be between about 1 m and 8 m. In some designs the length 140 of the pre-accelerator 108 is between about 3 m and 5 m and may be preferably about 4 m.

The drift tube linac section 112 can be referred to as a drift tube linac or drift tube structure. The drift tube linac section 112 may operate in a transmission magnetic (TM) mode and/or may operate in an energy range between about 1 MeV/u and 30 MeV/u or any range therebetween, such as 3 MeV/u and 20 MeV/u. The drift tube linac section 112 may include a plurality of gaps (e.g., multi-gap structure). For example, the drift tube linac section 112 may include between about 10 and 100 gaps, or between about 50 and 80 gaps, or about 65 gaps. The average electric field ($E_0$) and/or accelerating gradient ($E_0T$) may be substantially constant along a length 144 of the drift tube linac section 112. The average electric field may be between about 5 MV/m and 10 MV/m, and in some embodiments is about 8.6 MV/m. The accelerating gradient may be between about 6 MV/m and 7 MV/m. The length 144 of the drift tube linac section 112 can be between about 2 m and 11 m. In some designs the length 144 of the drift tube linac section 112 is between about 4 m and 8 m and may be preferably about 6 m.

The coupled drift tube linac section 116 may be referred to as a coupled drift tube linac or coupled drift tube element. The coupled drift tube linac section 116 can include one or more coupled drift tube structures or tanks. The one or more drift tube tanks can each include a plurality of gaps. For example, each structure can include between 4 and 8 gaps, and preferably include 6 gaps. The number of tanks in the coupled drift tube linac section 116 can be between about 6 and 15. For example, in certain embodiments the coupled drift tube linac section 116 includes 10 such tanks. The coupled drift tube linac section 116 may operate at an energy up to about 60 MeV/u. In some embodiments the coupled drift tube linac section 116 operates at an energy below about 45 MeV. The operating frequency of the coupled drift tube linac section 116 can be between about 300 MHz and 1400 MHz and in some embodiments is about 952 MHz. The coupled drift tube linac section 116 can include one or more FODO cells that may form a lattice. The lattice can include between about 50 T/m and 200 T/m, and preferably about 90 T/m, electromagnetic quadrupoles (EMQs). The EMQs may be disposed between the one or more drift tube tanks. Each of the one or more drift tube tanks can have identical cell lengths (e.g., within the tanks) and/or synchronous phase $\varphi_s$ equal to a negative phase (e.g., $\varphi_s=-90°$). The reference phase $\varphi_r$ (e.g., the average RF phase of the beam center in a given tank) can be lower in the first coupled drift tube structure (e.g., $\varphi_r=-24°$) than the last structure (e.g., $\varphi_r=-17°$). Phase slippage between adjacent tanks may be less than 10° and in some embodiments is less than about 7°. The length 148 of the coupled drift tube linac section 116 can be between about 2 m and 11 m. In some designs the length 148 of the coupled drift tube linac section 116 is between about 4 m and 8 m and may be preferably about 6 m.

The high gradient structure 118 can be configured to operate in a standing wave mode or a traveling wave mode. For embodiments that employ traveling wave mode, the traveling wave may be a forward traveling wave (FTW) or backward traveling wave (BTW). The high gradient structure 118 may include one or more structures or tanks. The number of tanks within the high gradient structure 118 can be up to 35 tanks. In some embodiments the number of tanks is 19. Focusing elements (e.g., quadrupole doublets) may be disposed between each of the one or more tanks. The length of each structure may vary based on its location within the high gradient structure 118. For example, longer tanks of the high gradient structure 118 may be disposed distal the coupled drift tube linac section 116 and/or shorter tanks may be disposed proximal the coupled drift tube linac section 116. The length L of each structure may be governed by the following equation:

$$\sigma_T^2 = \left[\frac{qGl\sqrt{LD}}{mc\gamma\beta}\right]^2 + \frac{\pi q E_0 T\sin(\varphi)P^2}{mc^2\lambda(\gamma\beta)^3}.$$

Each structure or tank in the high gradient structure 118 may include a plurality of accelerating cells, described in more detail herein. Each accelerating cell within the same structure may be substantially identical. Each structure may include between about 15 and 45 cells. In some embodiments, each structure includes between 20 and 36 cells. Tanks that are distal the coupled drift tube linac section 116 may include more cells and/or have greater lengths than the more proximal tanks. For example, some tanks (e.g., those proximal the particle source) may include between about 5 and 20 cells and preferably between about 12 and 18 cells. Other tanks (e.g., tanks distal the tanks that are proximal the particle source) may include more cells (e.g., more than 20 cells, more than 25 cells or more than 30 cells). Each tank may have cells that are of equal length within the tank. The length of each cell within a tank may dictate, in part, the beam velocity for which that tank is configured. Iris dimensions (e.g., iris diameter, iris thickness, etc.), described in more detail herein, may vary between cells of the same tank and/or between cells in different tanks.

In some embodiments, the reference phase $\varphi_r$ may be between about −15° and −30° and in some embodiments is approximately −20° substantially along one or more tanks of the high gradient structure 118 and, in some embodiments, along the whole length 152 of the high gradient structure 118. Phase slippage within a given tank may be no more than about 15° and in some embodiments is no more than about 7°. Phase advance between adjacent cells may be less than 180°. For example, the phase advance may be between about 120° and 150°. The length 152 of the high gradient structure 118 can be between about 15 m and 45 m. In some designs the length 152 of the high gradient structure 118 is between about 22 m and 30 m and may be preferably about 25 m. In contrast with many other linacs, such a short length can provide increased opportunity for construction of such devices. The reduced footprint and cost can make such linacs more available for use in, for example, medical device treatment centers, as disclosed in more detail herein.

Figure 2A:
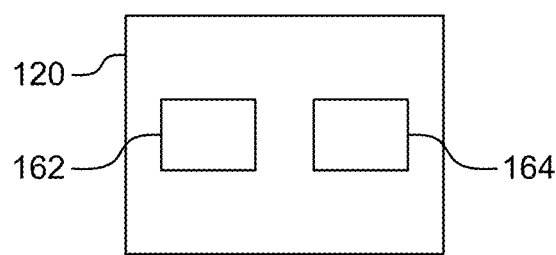
FIG. 2A shows a schematic of an example high gradient tank.
Figure 2B:
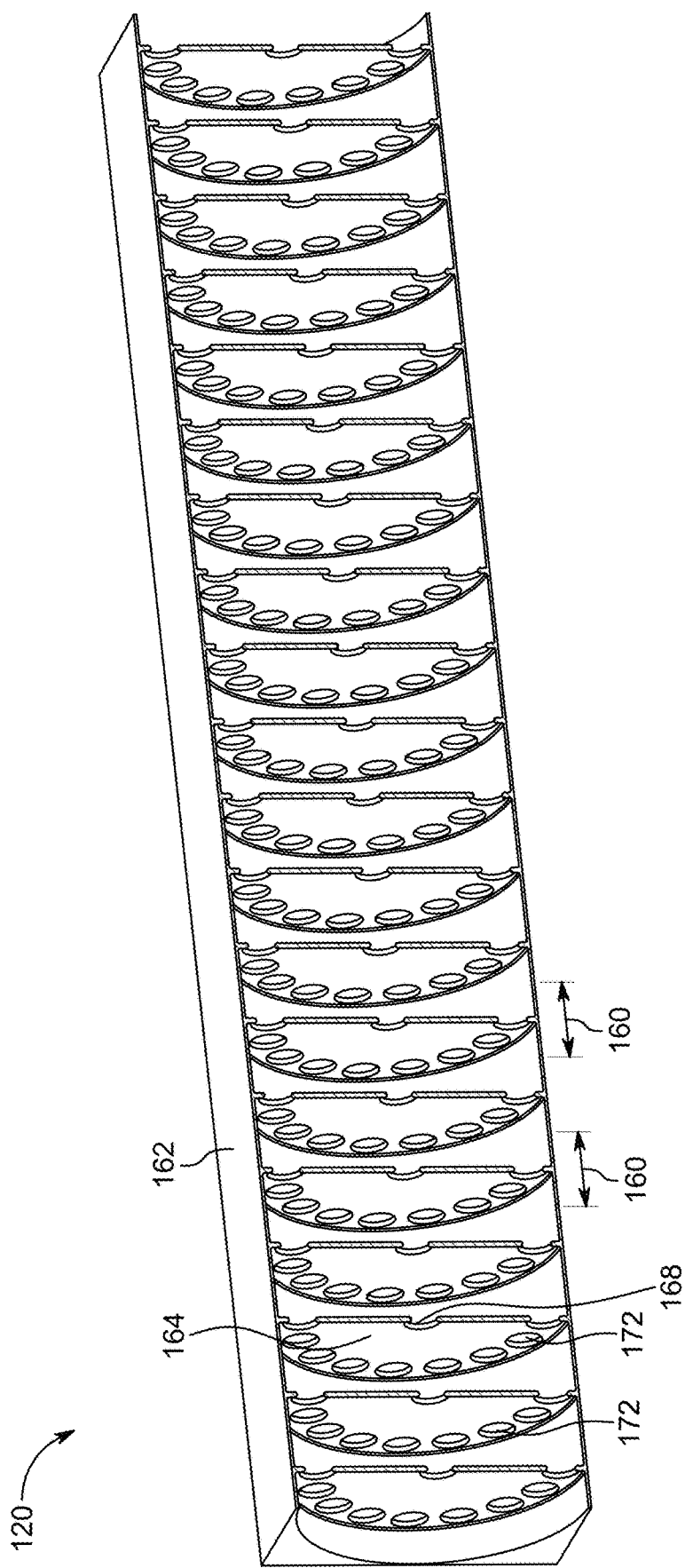
FIG. 2B shows an isometric view of a cross-section of a portion of an example configuration of a high gradient tank shown in FIG. 1A.

FIG. 2A shows a schematic of an example high gradient tank 120. The high gradient tank 120 may include a body 162 and one or more cell irises 164. The body 162 may include a plurality of body elements associated with each constituent cell element 200. FIG. 2B shows an isometric view of a cross-section of a portion of an example configuration of a high gradient tank 120 shown in FIG. 1A. As shown, the body 162 can be hollow and surround a plurality of cell irises 164. An outer cross-sectional shape of the body 162 can define one of a number of shapes. For example, the outer cross-sectional shape may be a rectangular prism (as shown), an ellipse, or any other shape. The body 162 can define a cavity in which the plurality of cell irises 164 are disposed. The cavity may be substantially ellipsoidal (e.g., circular) in cross-section (e.g., cross-section perpendicular to an optical path of the high gradient tank 120). The optical path of the high gradient tank 120 can define an optical axis. Each of the cell irises 164 can be disposed substantially perpendicular to the optical axis of the tank. Each of the cell irises 164 can include a plurality of iris holes 172 therein. For example, a plurality of iris holes 172 may be disposed near an edge of each cell iris 164. The plurality of iris holes 172 can be spaced approximately regularly from each other (e.g., equidistant from neighboring iris holes 172) around the cell iris 164. Each of the plurality of iris holes 172 may be circular in shape as shown. However, other shapes are possible as described herein. For example, irregular shapes (which may, for example, be regularly spaced about the cell iris 164) may be made to allow radiation to propagate according to dimensions specified herein. Such irregular shapes may include a washer-and-disk configuration described herein. Accordingly, in some embodiments, not every cell iris 164 includes the same shape, size, and/or spacing of iris holes 172 within the cell iris 164. The number of iris holes 172 can range from between 2 holes and 24 holes. Preferably the number of iris holes 172 is between 8 and 20. In certain preferred embodiments, the number of iris holes 172 is 16. The high gradient tank 120 (e.g., each cell 160 therein) may comprise copper and/or other metal (e.g., silver, gold). The metal (e.g., copper) may be annealed to provide greater resistance to the stresses it may undergo during use of the linear accelerator 100 and/or high gradient structure 118. In some embodiments, each cell may be attached to neighboring cells using a welding or brazing technique. In such embodiments, as an example, other metals or alloys may be included in the high gradient tank 120 (e.g., in the joints between cells).

In some embodiments, each of the cell irises 164 includes an iris aperture 168. The iris aperture 168 may be disposed about the optical axis of the high gradient tank 120. One or more of the iris apertures 168 of the cell irises 164 can include a nose (not shown in FIG. 2B), as described more fully herein. The high gradient tank 120 can include a plurality of cells 160. Each cell may have a length defined along the optical axis of the tank. In some embodiments and/or in some high gradient tanks 120 of a multiple-tank embodiment, the cells 160 can have equal length, for example, within the same high gradient tank 120. Other configurations (e.g., increasing lengths of cells, decreasing lengths of cells, alternating lengths of cells) are possible.

The starting and ending points of each cell within the high gradient tank 120 may be defined in a number of ways. For example, the cells 160 may be measured such that each cell starting and/or ending point is equidistant between the two nearest cell irises 164. This can make sense, for example, in embodiments where each cell 160 consists of a single manufactured (e.g., molded, machined) element. In such embodiments, cells 160 may be attached to each other (e.g., welded, brazed) to create the high gradient tank 120. In such embodiments, each cell element includes a portion of the body 162 as well as the corresponding cell iris 164. More details on such embodiments are described herein.

Figure 2C:
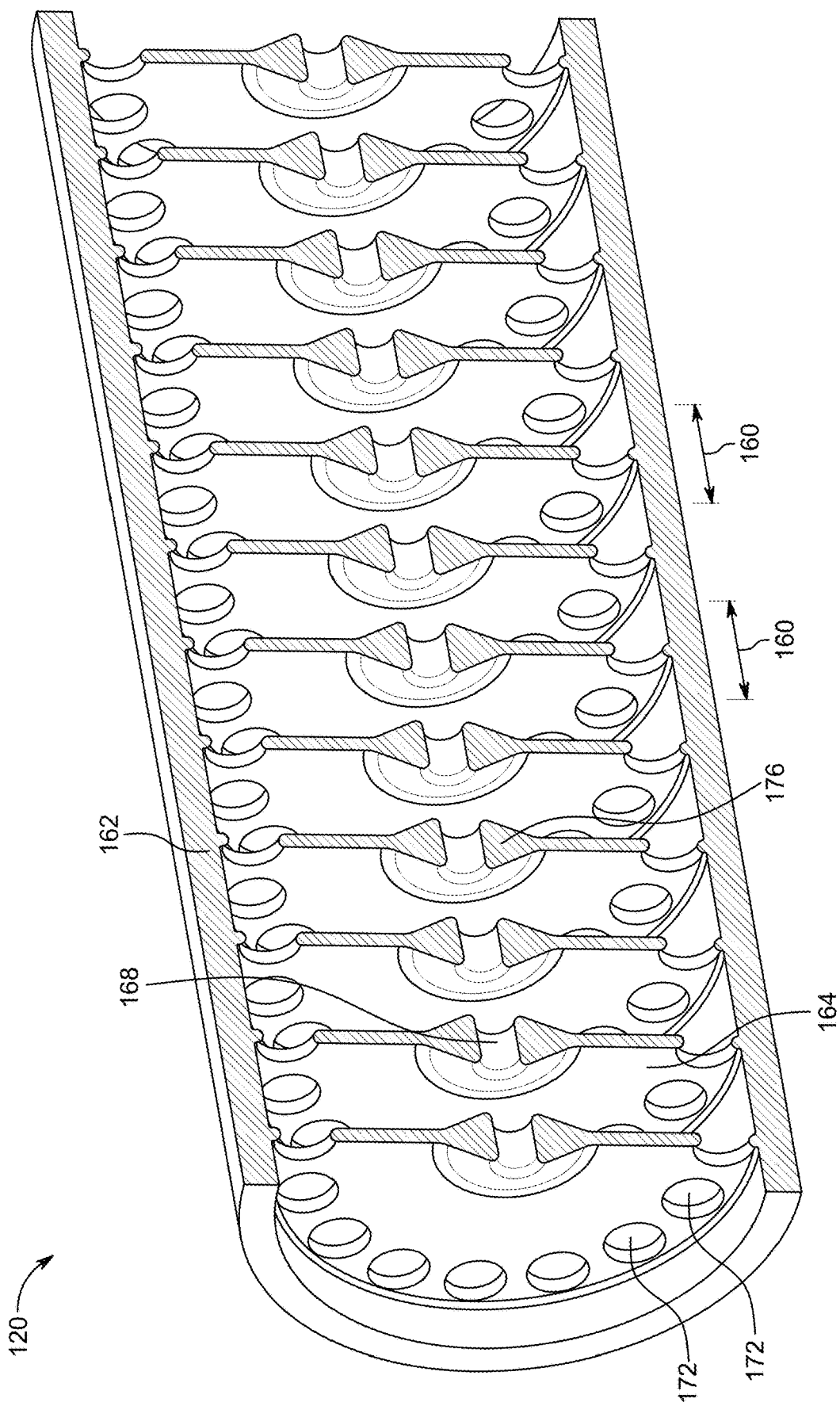
FIG. 2C shows an example high gradient tank with cell irises that include iris noses.

FIG. 2C shows an example high gradient tank 120 with cell irises 164 that include iris noses 176. As is described in more detail herein, each nose may include increasing thickness in the corresponding cell iris 164 radially along a portion of the cell iris 164, as shown. Just radially from the iris aperture 168 of the corresponding cell iris 164, the iris nose 176 may include a decrease in thickness of the cell iris 164. Accordingly, a cross-section of the iris nose 176 can include opposing nose-shaped structures. Details of various embodiments of such noses are described in more detail herein.

Figure 3A:
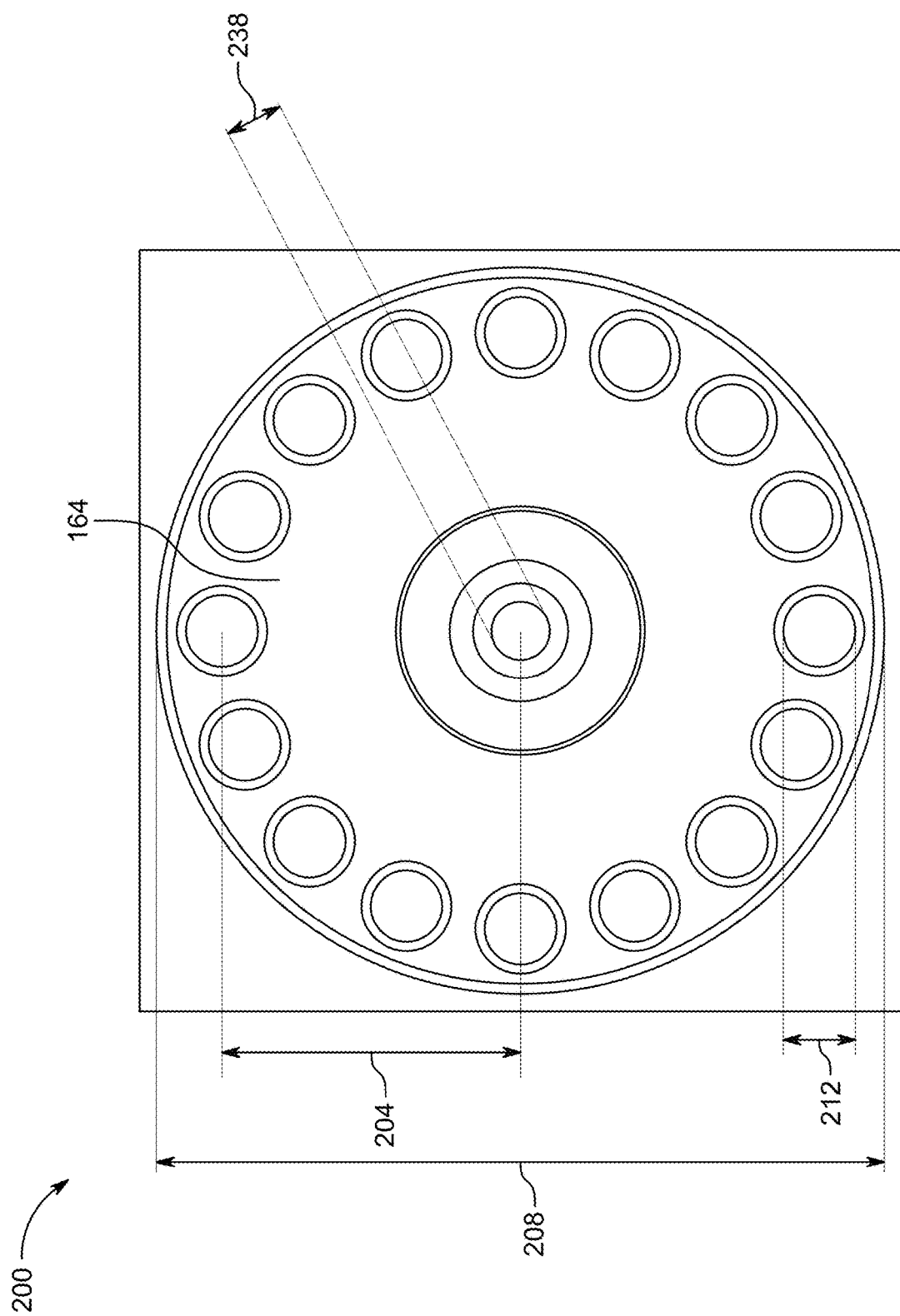
FIG. 3A shows a front view of a cell element.
Figure 3C:
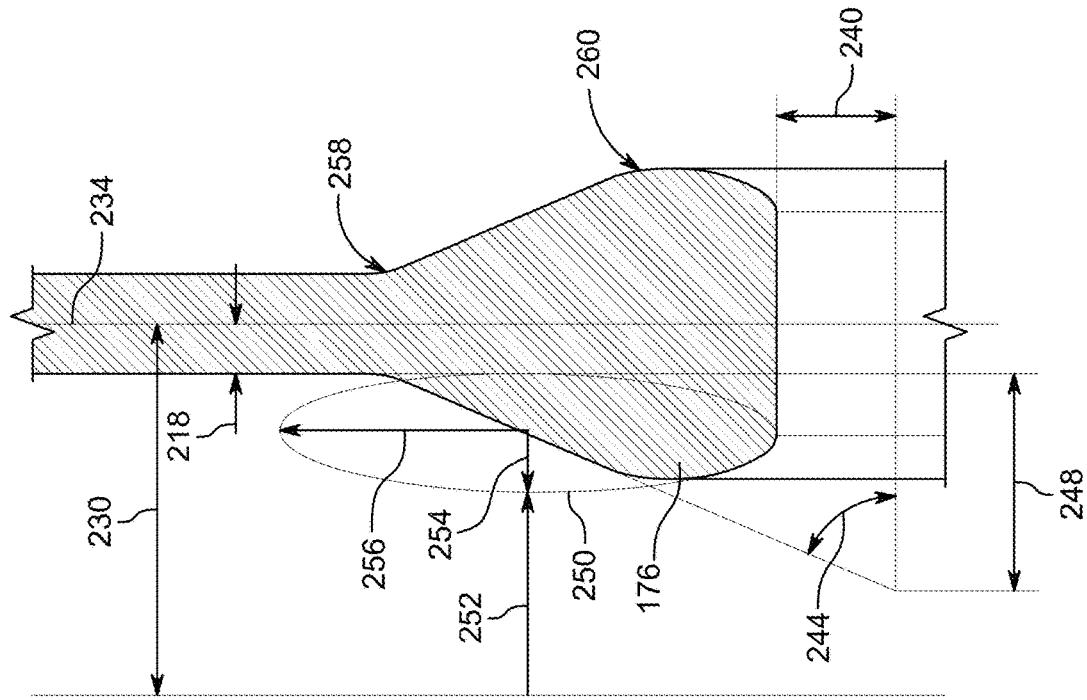
FIG. 3C shows another cross-sectional side view with additional dimensions of the example cell element shown in FIGS. 3A-3B with particular reference to various dimensions of the iris nose.
Figure 3B:
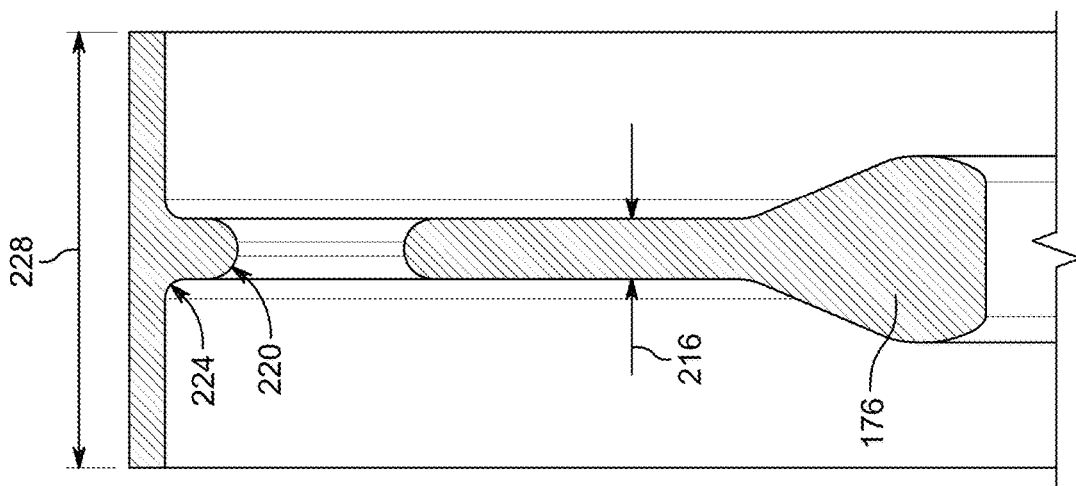
FIG. 3B shows a cross-sectional side view of a portion of a cell element with an iris nose.
Figure 4C:
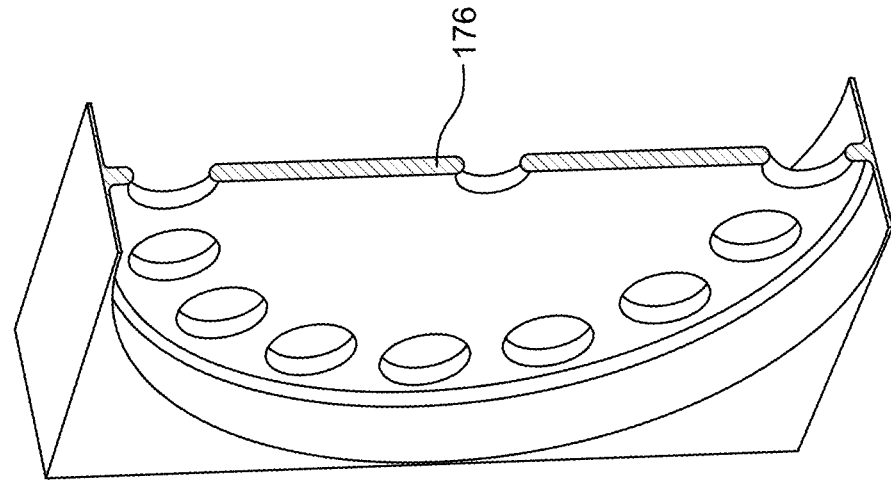
FIG. 4C shows a cross-sectional side view of an example of an iris nose that may be used.
Figure 4B:
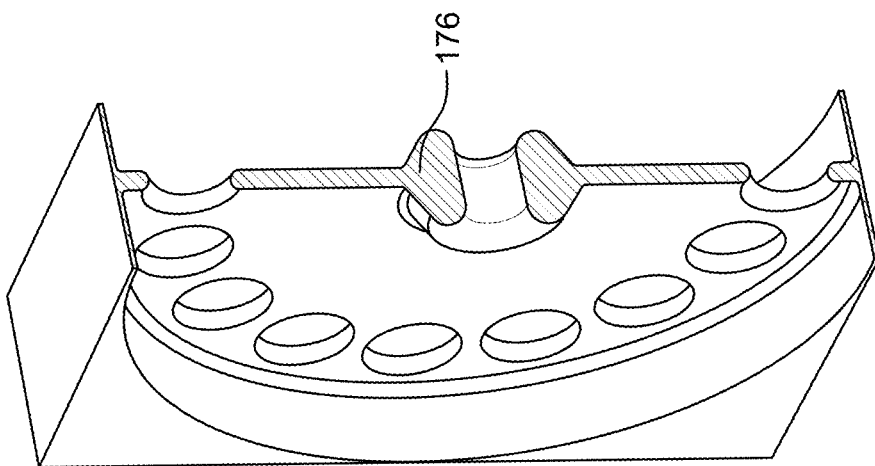
FIG. 4B shows a cross-sectional side view of an example of an iris nose that may be used.
Figure 4A:
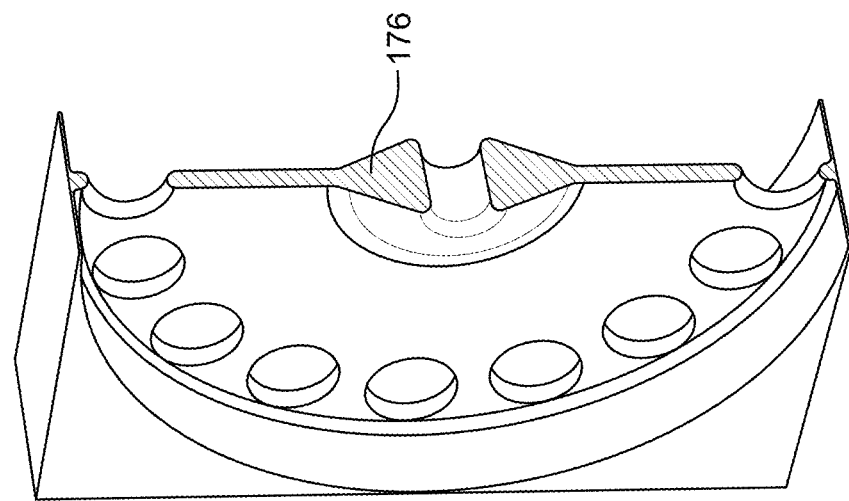
FIG. 4A shows a cross-sectional side view of an example of an iris nose that may be used.
Figure 4F:
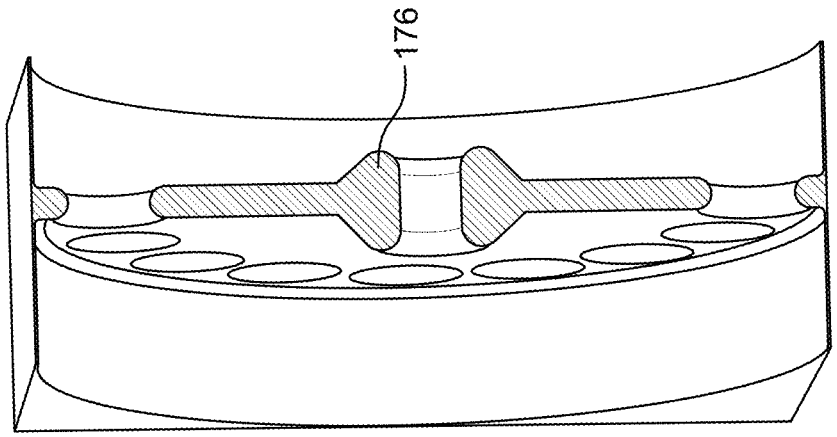
FIG. 4F shows a cross-sectional side view of an example of an iris nose that may be used.
Figure 4E:
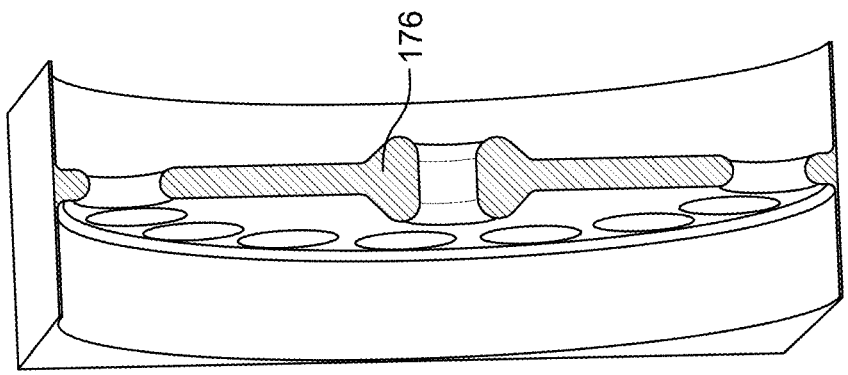
FIG. 4E shows a cross-sectional side view of an example of an iris nose that may be used.
Figure 4D:
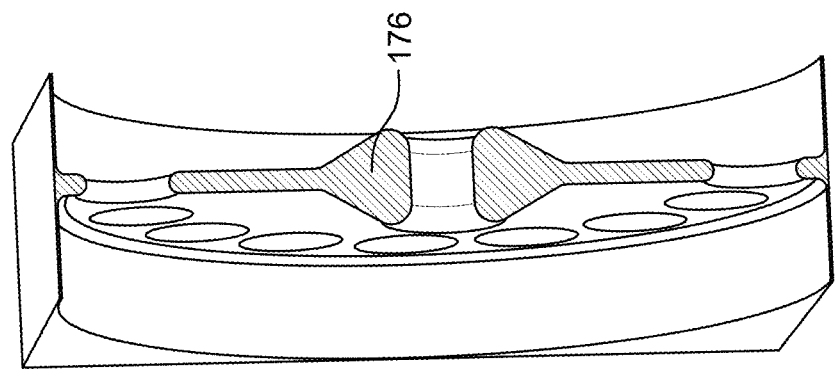
FIG. 4D shows a cross-sectional side view of an example of an iris nose that may be used.

FIGS. 3A-3C illustrate various dimensions of an example cell element 200. FIG. 3A shows a front view of a cell element 200. As shown the cell element 200 has a square outer shape, but other shapes are possible (e.g., circle, rectangular, etc.). The cell diameter 208 can be between about 45 mm and 165 mm and in some embodiments is between about 60 mm and 90 mm. In some embodiments the cell diameter 208 is about 74.5 mm.

The hole orbit radius 204 can be between about 8 mm and 70 mm and in some embodiments is between about 18 mm and 42 mm. In some embodiments the hole orbit radius 204 is about 30 mm. A ratio of cell diameter 208 to hole orbit radius 204 may be between about 2 and 3 and in some embodiments is about 2.5.

The hole diameter 212 can be between about 2 mm and 18 mm and in some embodiments is between about 5 mm and 12 mm. In some embodiments the hole diameter 212 is about 8 mm. The aperture diameter 238 can be between about 1.5 mm and 14 mm and in some embodiments is between about 4 mm and 10 mm. In some embodiments the aperture diameter 238 is about 6 mm. A ratio of hole diameter 212 to aperture diameter 238 may be between about 0.75 and 2.5 and in some embodiments is about 1.3.

FIG. 3B shows a cross-sectional side view of a portion of a cell element 200 with an iris nose 176. A cell length 228 can be between about 6 mm and 6 cm and in some embodiments is between about 12 mm and 85 mm. In some embodiments the cell length 228 is about 18 mm. The cell length 228 may be referred to as a structure period. The cell length 228 may be measured from a middle of a cell iris 164 to the middle of a subsequent cell iris 164. In some cases, the cell length 228 may be measured between midpoints between cell irises 164. An iris thickness 216 can be between about 0.5 mm and 5 mm and in some embodiments is between about 1 mm and 5 mm. In some embodiments the iris thickness 216 is about 2.5 mm. A ratio of the cell length 228 to the iris thickness 216 can be between about 3 and 12 and in some embodiments is between about 5 and 10. In some embodiments the ratio is about 7. A ratio of the cell diameter 208 to the cell length 228 can be between about 1 and 10 and in some embodiments is between about 2 and 6. In some embodiments, the ratio is about 4.

A hole blend radius 220 can be between about 0.3 mm and 3 mm and in some embodiments is between about 0.5 mm and 2 mm. In some embodiments the hole blend radius 220 is about 1 mm. A cell blend radius 224 can be between about 0.3 mm and 3 mm and in some embodiments is between about 0.5 mm and 2 mm. In some embodiments the cell blend radius 224 is about 1 mm. A ratio of the hole blend radius 220 to the cell blend radius 224 can be between about 0.5 and 2 and in some embodiments is about 1.

FIG. 3C shows another cross-sectional side view with additional dimensions of the example cell element 200 shown in FIGS. 3A-3B with particular reference to various dimensions of the iris nose 176. The cell iris 164 can define an iris plane 234 about which some of the dimensions are based. The iris plane 234 can be perpendicular to an optical axis of the cell element 200. A cell half-length 230 is shown for reference. The aperture radius 240 is also shown for context. Similarly, the iris half-thickness 218 is shown.

The iris nose 176 can be described using one or more of a number of dimensions as shown in FIG. 3C. A slope of the iris nose 176 can be described by a nose rise angle 244, which is shown at the intersection of an aperture-bisecting line and a line tracing a rise of the iris nose 176. The nose rise angle 244 can be between about 35° and 90° (e.g., no nose at all) and in some embodiments is between about 50° and 75°. In some embodiments the nose rise angle 244 is about 66°. A blend between horizontal and the rise of the iris nose 176 can be described using a nose ellipse 250 as shown. The nose ellipse 250 can have a transversal radius 256 and a longitudinal radius 254. The longitudinal radius 254 can be between about 0.5 mm and 12 mm and in some embodiments is between about 0.8 mm and 3 mm. In some embodiments the longitudinal radius 254 is about 1.4 mm. The transversal radius 256 can be between about 2 mm and 30 mm and in some embodiments is between about 4 mm and 20 mm. In some embodiments the transversal radius 256 is about 6 mm. A ratio of the transversal radius 256 and the longitudinal radius 254 can be between about 0.5 and 10 and in some embodiments is between about 2 and 7. In some embodiments the ratio is about 4. A half-gap 252 between nose ellipses 250 of adjacent cells 160 can be between about 2 mm and 10 mm and in some embodiments is about 5 mm. A maximum thickness of the iris nose 176 can be between about 2 mm and 15 mm and in some embodiments is between about 4 mm and 11 mm. In some embodiments the maximum thickness of the iris nose 176 is about 8 mm. A ratio of the maximum thickness of the iris nose 176 and the iris thickness 216 is between about 1 (no nose) and 8 and in some embodiments is between about 2 and 5. In some embodiments, the ratio is about 3.

The nose concave blend radius 258 can be between about 1 mm and 10 mm and in some embodiments is between about 2 mm and 8 mm. In some embodiments the nose concave blend radius 258 is about 4 mm. The nose convex blend radius 260 can be between about 0.3 mm and 10 mm and in some embodiments is between about 0.7 mm and 6 mm. In some embodiments the nose convex blend radius 260 is about 1 mm. A ratio between the nose concave blend radius 258 and the nose convex blend radius 260 can be between about 1 and 10 and in some embodiments is about 4.

FIGS. 4A-4F show cross-sectional side views of various examples of iris noses 176 that may be used.

Figure 5:
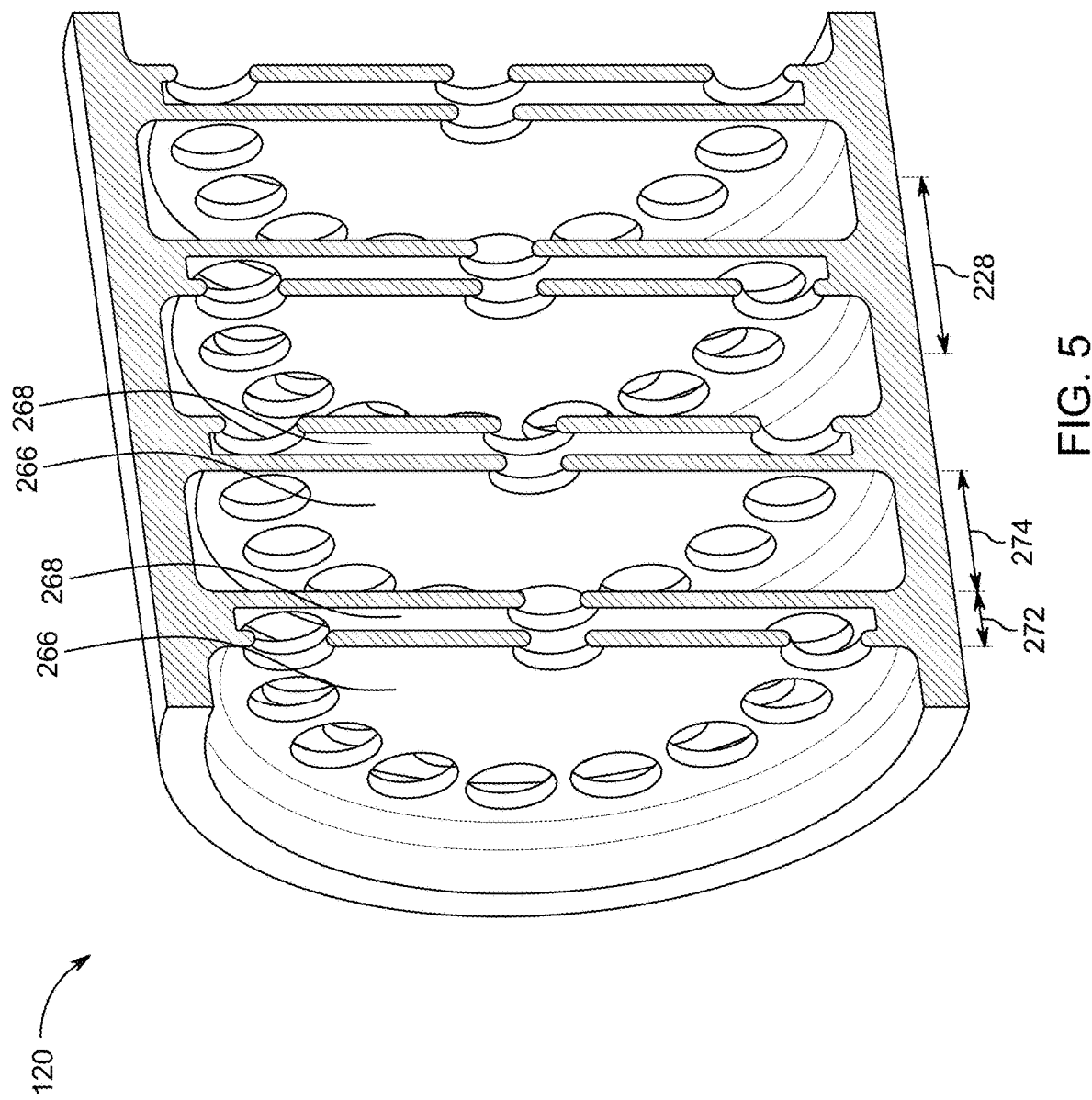
FIG. 5 shows an example portion of a high gradient tank that includes a bi-periodic accelerating structure.

FIG. 5 shows an example portion of a high gradient tank 120 that includes a bi-periodic accelerating structure. The high gradient tank 120 may include a plurality of leading irises 266 and corresponding trailing irises 268. These irises 266, 268 may thus define a short distance 272 between irises and a long distance 274 between irises. A total cell length 228 of the cells 160 can comprise a sum of the short distance 272 and the long distance 274. A ratio of the long distance 274 to the short distance 272 can be between about 1 and 20 and in some embodiments is between about 1.5 and 8. In some embodiments the ratio is about 5.

Figure 6:
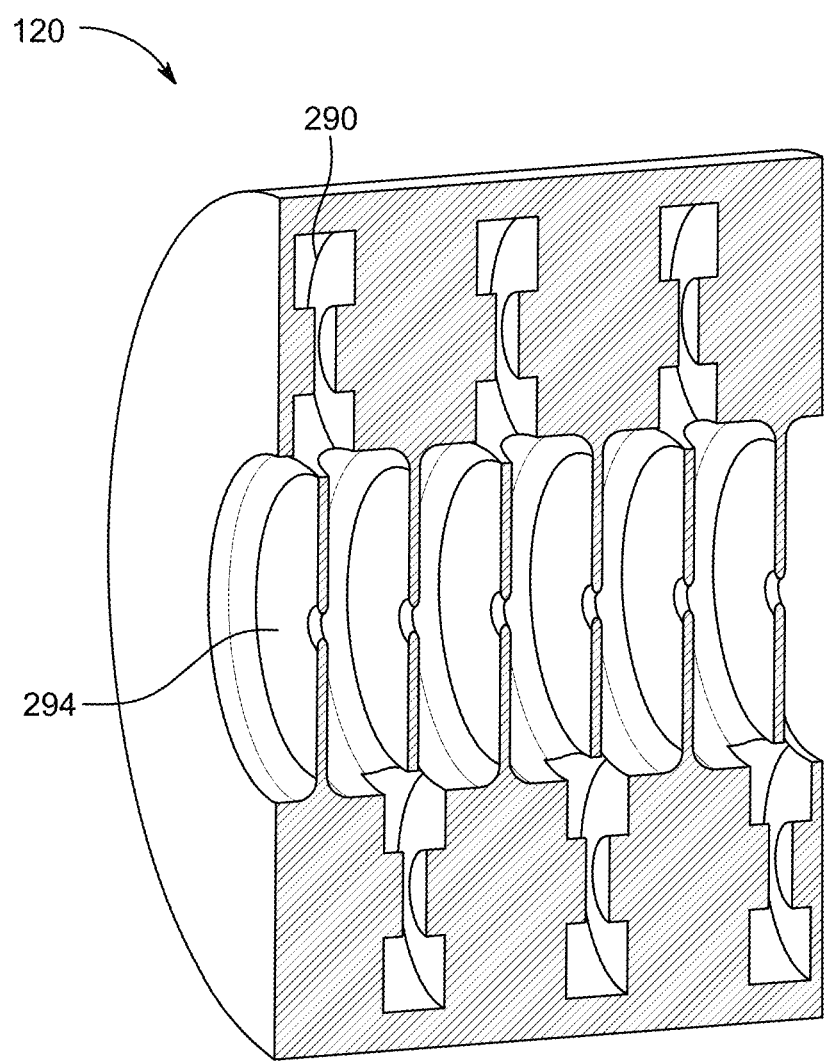
FIG. 6 shows an example portion of a high gradient tank that includes coupling cells.

FIG. 6 shows an example portion of a high gradient tank 120 that includes coupling cells 290. The coupling cells 290 may be disposed regularly along one or more sides of the accelerating cells 294 and may therefore be referred to as side coupling cells. Consecutive coupling cells 290 may alternate sides of the accelerating cells 294. The side coupling cells may be tuned using, for example, tuning studs. Additional details of tuning and coupling cells can be found in U.S. patent application Ser. No. 15/933,257, which is hereby incorporated by reference herein in its entirety for all purposes.

Figure 7:
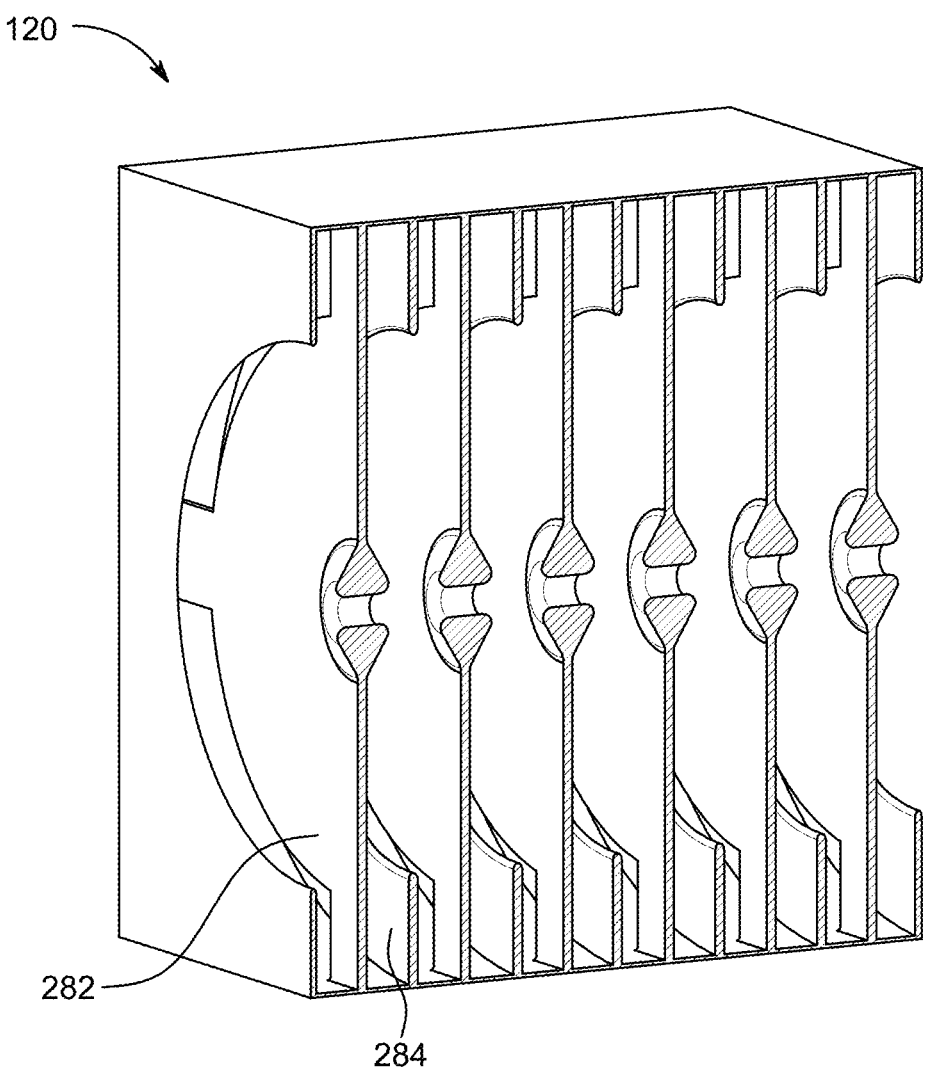
FIG. 7 shows an example portion of a high gradient tank that includes alternating cell disks and cell washers.

FIG. 7 shows an example portion of a high gradient tank 120 that includes alternating cell disks 282 and cell washers 284. This so-called disk-and-washer arrangement can be implanted in whole or in part with other aspects of the features described herein. Consecutive cell disks 282 and/or cell washers 284 can be spaced regularly from one another along the optical axis of the high gradient tank 120. In some embodiments portions of the cell disks 282 near the body 162 may be removed and/or omitted in manufacture, as shown. These portions may approximate the size and/or shape of the neighboring cell washers 284.

Figure 8A:
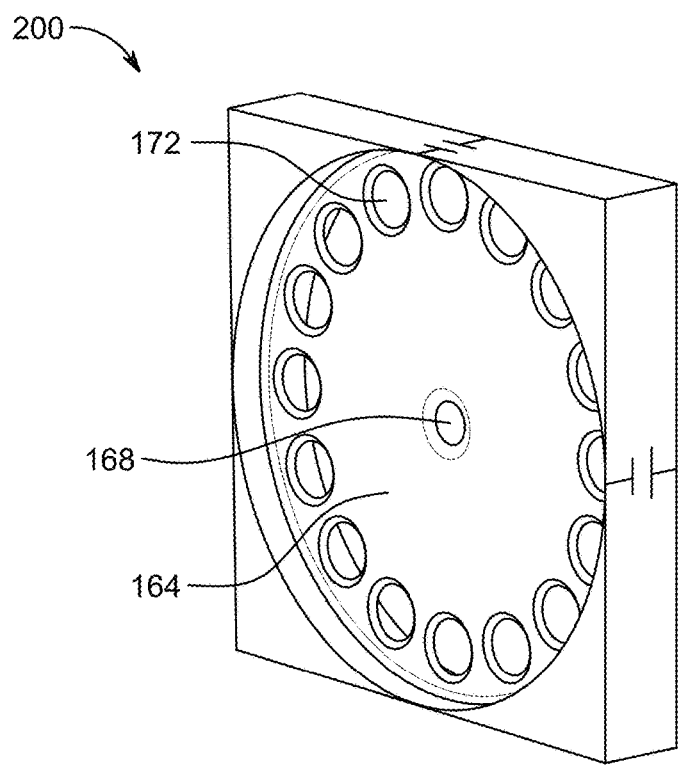
FIG. 8A shows an isometric view of an example cell element without a nose cone.
Figure 8B:
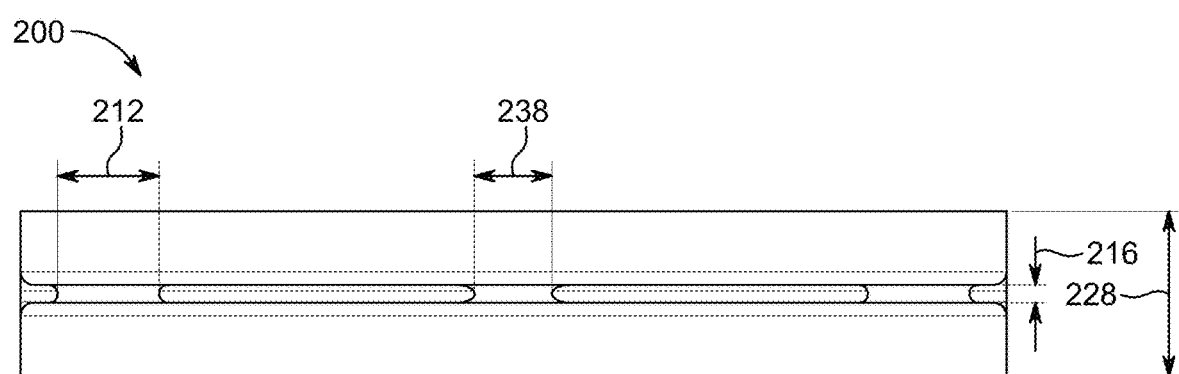
FIG. 8B shows a cross-sectional side view of the cell element of FIG. 8A.

FIG. 8A shows an isometric view of an example cell element 200 without a nose cone. FIG. 8B shows a cross-sectional side view of the cell element 200 of FIG. 8A. The cell element 200 may be used, for example, in a BTW structure and/or may operated at a fundamental harmonic with $\beta=0.3$.

Figure 9:
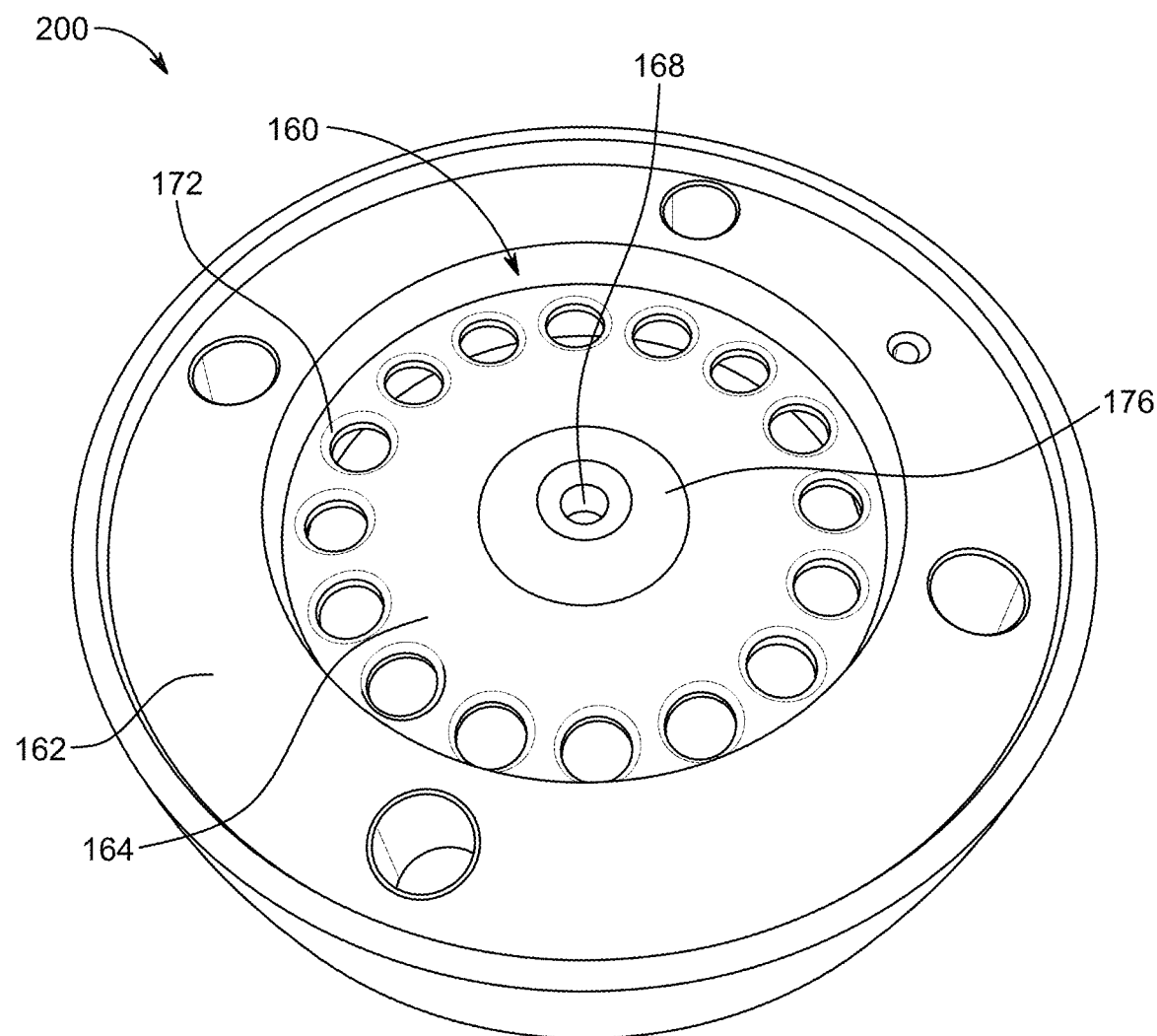
FIG. 9 illustrates a manufactured example of a cell element.

FIG. 9 illustrates a manufactured example of a cell element 200.

Figure 10:
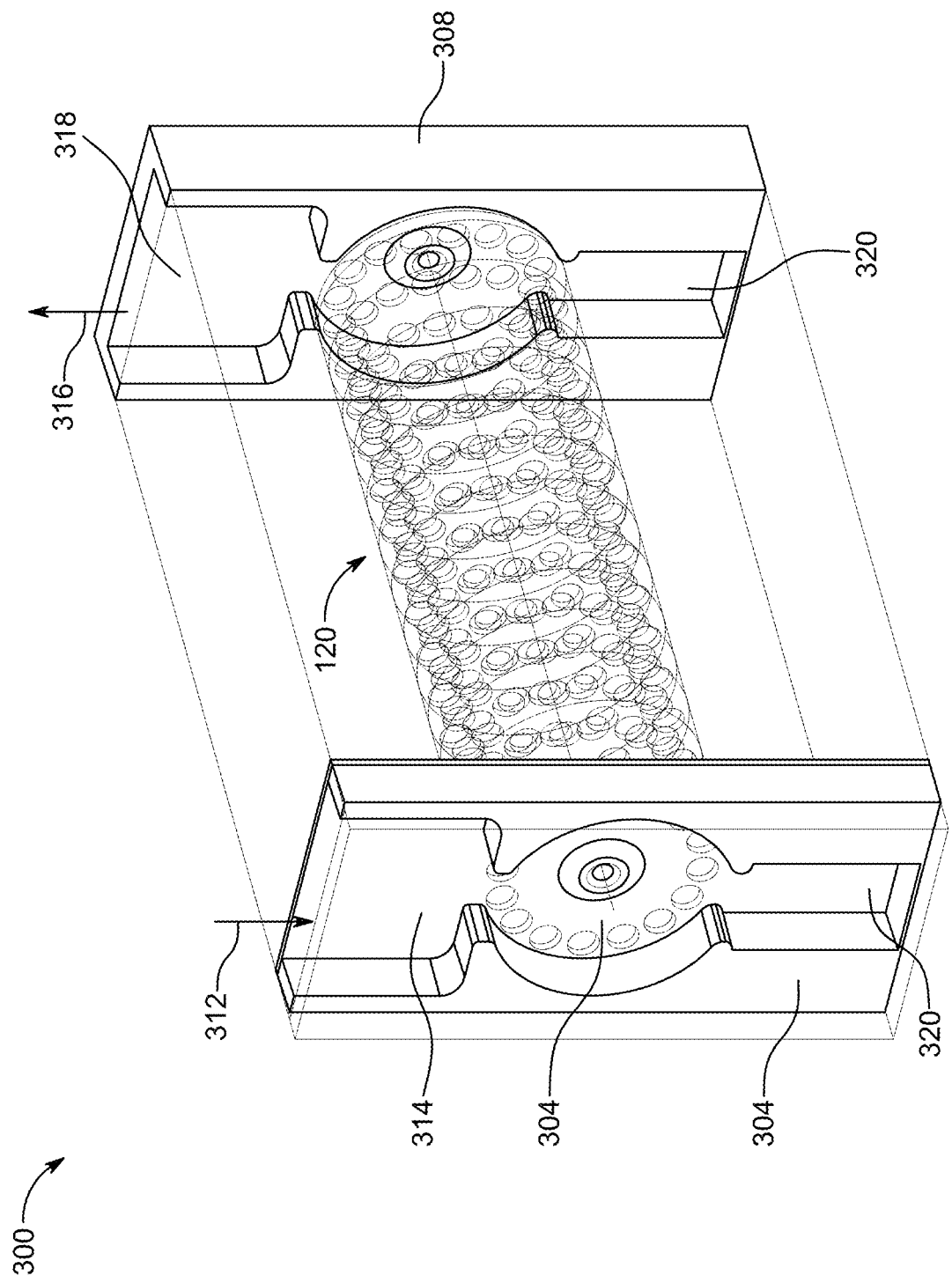
FIG. 10 shows an isometric view of an example vacuum port and RF power coupler arrangement.

FIG. 10 shows an isometric view of an example vacuum port and RF power coupler arrangement 300. One or more power coupler cells 304, 308 can be included, for example, at periodic intervals along the high gradient structure 118. For example, power couplers cells may be disposed between each high gradient tank 120 in the high gradient structure 118. The high gradient tank 120 can be disposed between the power coupler cells 304, 308, as shown. A coupler cell may be included at both the beginning and end of the tank for traveling wave (TW) tanks (e.g., FTW, BTW). A single coupler cell may be included in tanks for standing wave (SW) tanks. In such SW tanks, the coupler cell may be disposed at the end (e.g., distal end) of the tank. The input power coupler cell 304 can include an RF power input port 314 configured to receive RF power input 312. An RF power window 338 can be disposed between the RF power input port 314 and the input power coupler cell 304. The input power coupler cell 304 can be disposed about the optical axis of the high gradient tank 120. A vacuum port 320 can be disposed within the input power coupler cell 304. The vacuum port 320 may be disposed opposite the RF power input port 314. The vacuum port 320 can be configured for fluid communication with a vacuum pump (not shown). Each vacuum port 320 can be configured to achieve a vacuum conductance such that an effective pumping speed of greater than 25 L/s can be achieved. Due to the geometries described herein, the vacuum port 320 and/or the cells 160 in the high gradient tank 120 can be configured to allow the vacuum pump to achieve an effective pumping speed of greater than 47 L/s and in some embodiments greater than or equal to 55 L/s. In certain embodiments, the effective pumping speed can be greater than 65 L/s. The output power coupler cell 308 may have one or more dimensions that are the same as the input power coupler cell 304. In some embodiments, the input power coupler cell 304 and the output power coupler cell 308 are substantially identical. This can reduce errors and/or costs in manufacture.

Figure 11:
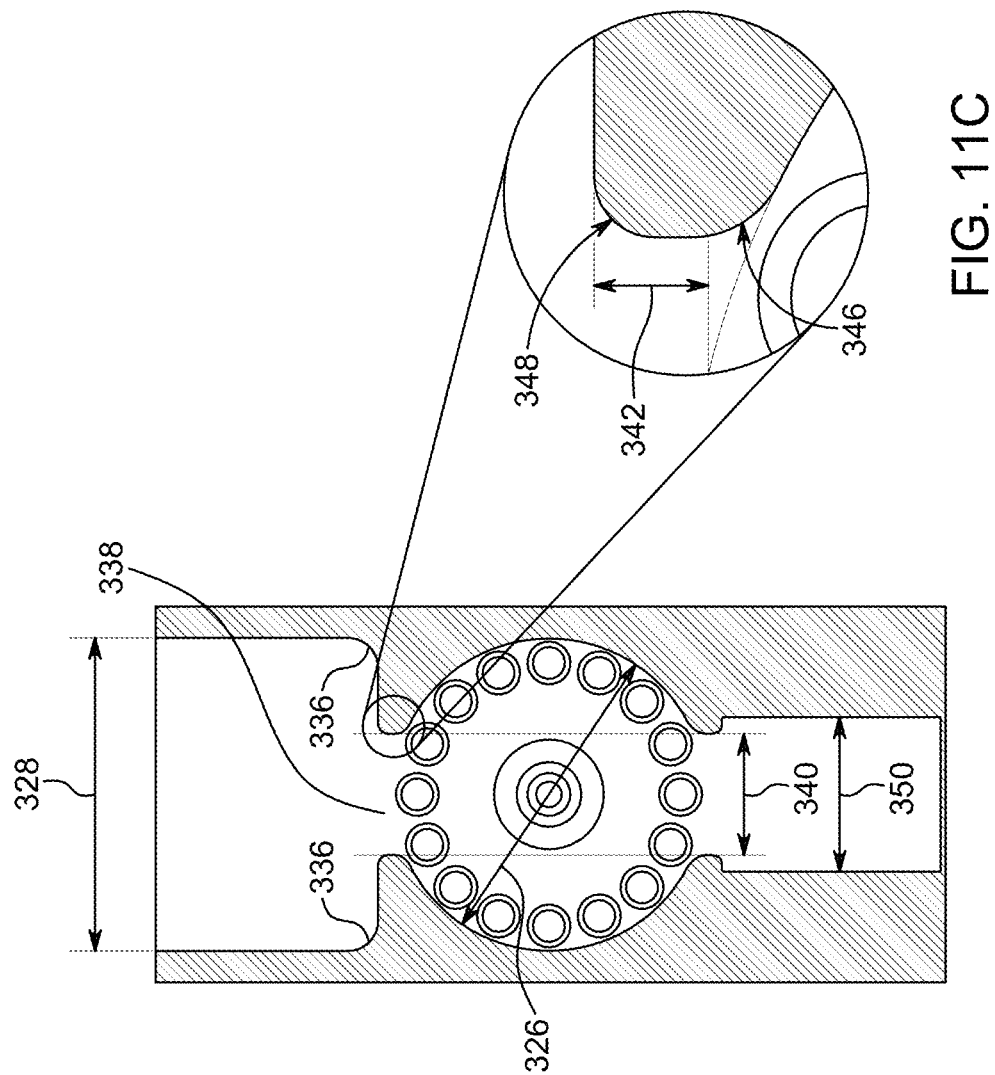
FIG. 11A shows a cross-sectional side view of the coupler cell.
FIG. 11B shows a cross-sectional front view of the example power coupler cell of FIG. 11A.
FIG. 11C shows a detail view of a portion of view shown in FIG. 11B.

FIGS. 11A-11C illustrates various dimensions of an example power coupler cell 304, 308. FIG. 11A shows a cross-sectional side view of the coupler cell. The coupler cell length 324 may be between about 5 mm and 50 mm and in some embodiments is about 18 mm. The coupler cell may include a cell iris, an iris aperture, and/or one or more iris holes. Each of these may have dimensions described with respect to the accelerating cells and/or the high gradient tank 120 herein.

FIG. 11B shows a cross-sectional front view of the example power coupler cell 304, 308 of FIG. 11A. The coupler cell diameter 326 can be between about 45 mm and 160 mm and in some embodiments is between about 60 mm and 90 mm. In some embodiments the coupler cell diameter 326 is about 72 or 73 mm. The coupler cell diameter 326 may be greater in the output power coupler cell 308 than in the input power coupler cell 304. The RF power window width 340 can be between about 8 mm and 50 mm and in some embodiments is between about 18 mm and 32 mm. In some embodiments the RF power window width 340 can be about 25 mm or 26 mm.

A vacuum port width 350 can be between about 5 mm and 60 mm and in some embodiments is between about 15 mm and 40 mm. In some embodiments the vacuum port width 350 is about 35 mm. An RF power port width 328 can be between about 30 mm and 150 mm and in some embodiments is between about 50 mm and 80 mm. In some embodiments the RF power port width 328 is about 72 mm. A ratio of the RF power port width 328 to the RF power window width 340 can be between about 1 to 15 and in some embodiments is between about 1.5 and 7. In some embodiments the ratio is about 2. An RF power port blend radius 336 can be between about 1 mm and 15 mm and in some embodiments is between about 3 mm and 10 mm. In some embodiments the RF power port blend radius 336 is about 7 mm.

FIG. 11C shows a detail view of a portion of view shown in FIG. 11B. A window inner blend radius 346 can be between about 1 mm and 50 mm and in some embodiments is between about 2 mm and 35 mm. In some embodiments the window inner blend radius 346 is about 3 mm. A window outer blend radius 348 can be between about 1 mm and 70 mm and in some embodiments is between about 1.5 mm and 50 mm. In some embodiments the window outer blend radius 348 is about 2 mm. A window thickness 342 can be defined as shown, such as from a top of the input power coupler cell 304. The window thickness 342 can be between about 1 mm and 25 mm and in some embodiments is between about 2 mm and 15 mm. In some embodiments the window thickness 342 is about 4 mm.

Figure 12:
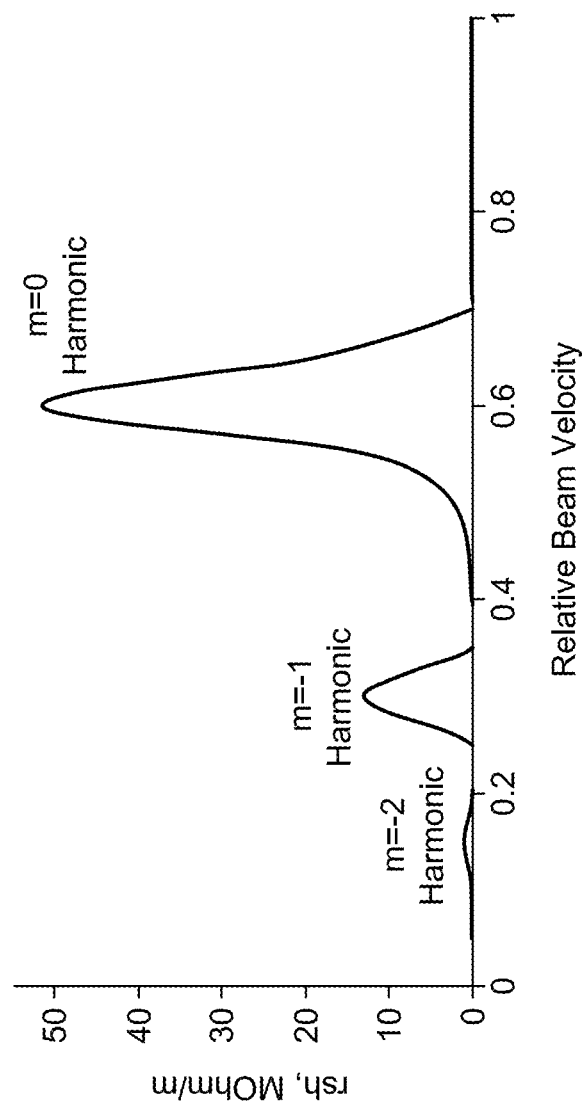
FIG. 12 shows the shunt impedance that can be achieved for $\beta=0.3$ cells (without noses) and a relative beam velocity ($\beta$) at a fundamental harmonic structure (FHS) and various negative harmonic structures (NHS).

FIG. 12 shows the shunt impedance ($r_{sh}$) (MΩ/m) that can be achieved at an operating frequency of 2856 MHz for $\beta$=0.3 cells (without noses) and a relative beam velocity ($\beta$) at a fundamental harmonic structure (FHS) and various negative harmonic structures (NHS). As shown, the amplitudes of higher harmonics can reduce dramatically, so the resulting shunt impedance of the 2π/3 FHS can be about 1.5 times higher than the shunt impedance of the 2π/3 first NHS. To compensate the reduced energy gain due to the smaller amplitude, noses (as described herein) can be introduced in the NHS that can concentrate the electric field near the beam axis and improve the shunt impedance.

Figure 13:
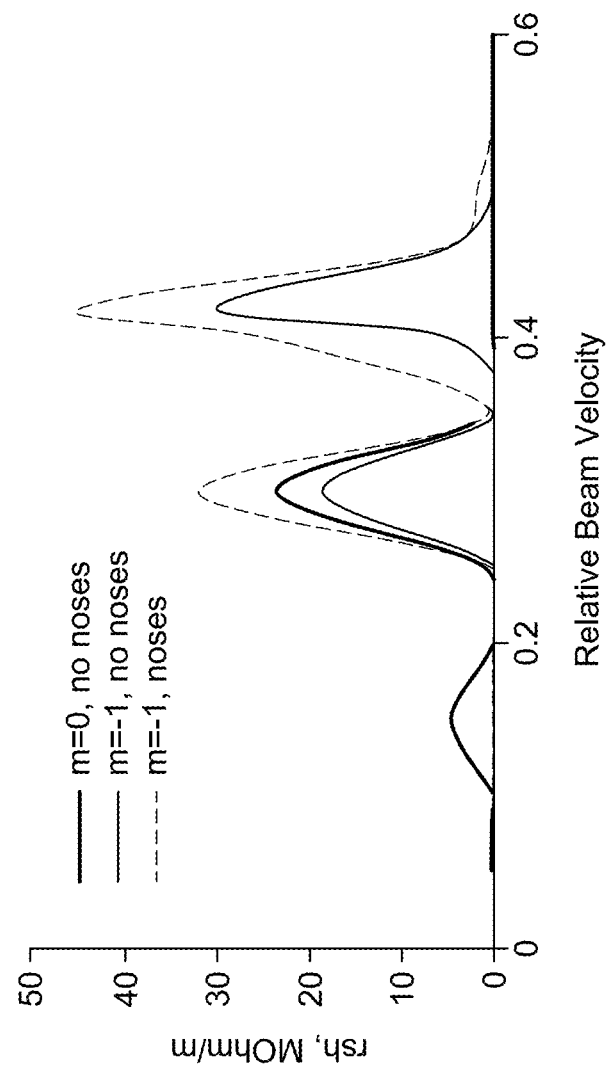
FIG. 13 shows the shunt impedance that can be achieved for various harmonics with noses vs some without noses.

FIG. 13 shows the shunt impedance that can be achieved for various harmonics with noses vs some without noses. Each nose can have an elliptical profile, as described herein, to minimize the surface electric field on it. The nose profile may be formed by a cylindrical surface and by the intersection of an ellipse with a cone. Magnetic coupling between cells can be performed with 16 holes in the iris with, for example, uniform angular spacing. The number of holes can be greater than 2, greater than 4, preferably greater than 6, and more preferably greater than 12. Shunt impedance can be increased while a ratio of peak electric field to the accelerating gradient $E_{max}/E_{acc}$ may be kept below 3.5, below 3.2, and/or in some embodiments below about 3.1. This can correspond to a surface electric field of up to about 160 MV/m or more.

Figure 14:
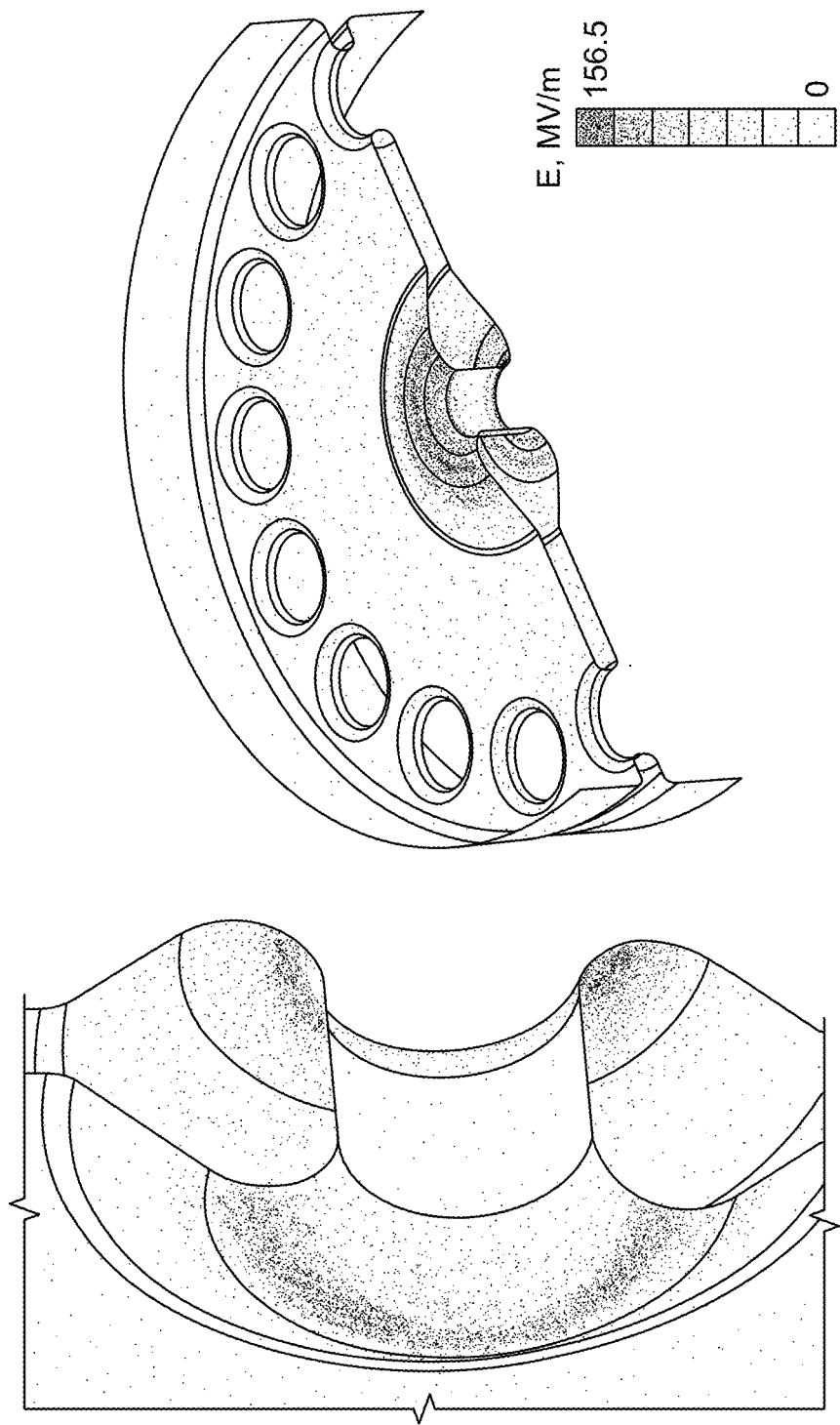
FIG. 14 shows an example distribution of electric field strength in some high gradient cells and in a detail of the nose.

FIG. 14 shows an example distribution of electric field strength (E) (MV/m) in some high gradient cells 160 and in a detail of the nose. As shown, the electric field strength generally increases closer to the iris aperture. The electric field strength may be at a maximum near the iris nose. The maximum electric field strength may be less than 160 MV/m and may be about 156 MV/m or less. Accordingly, the design peak electric field strength may be lower than the 160 MV/m RF breakdown (RFBD) limit in S-band.

Figure 15:
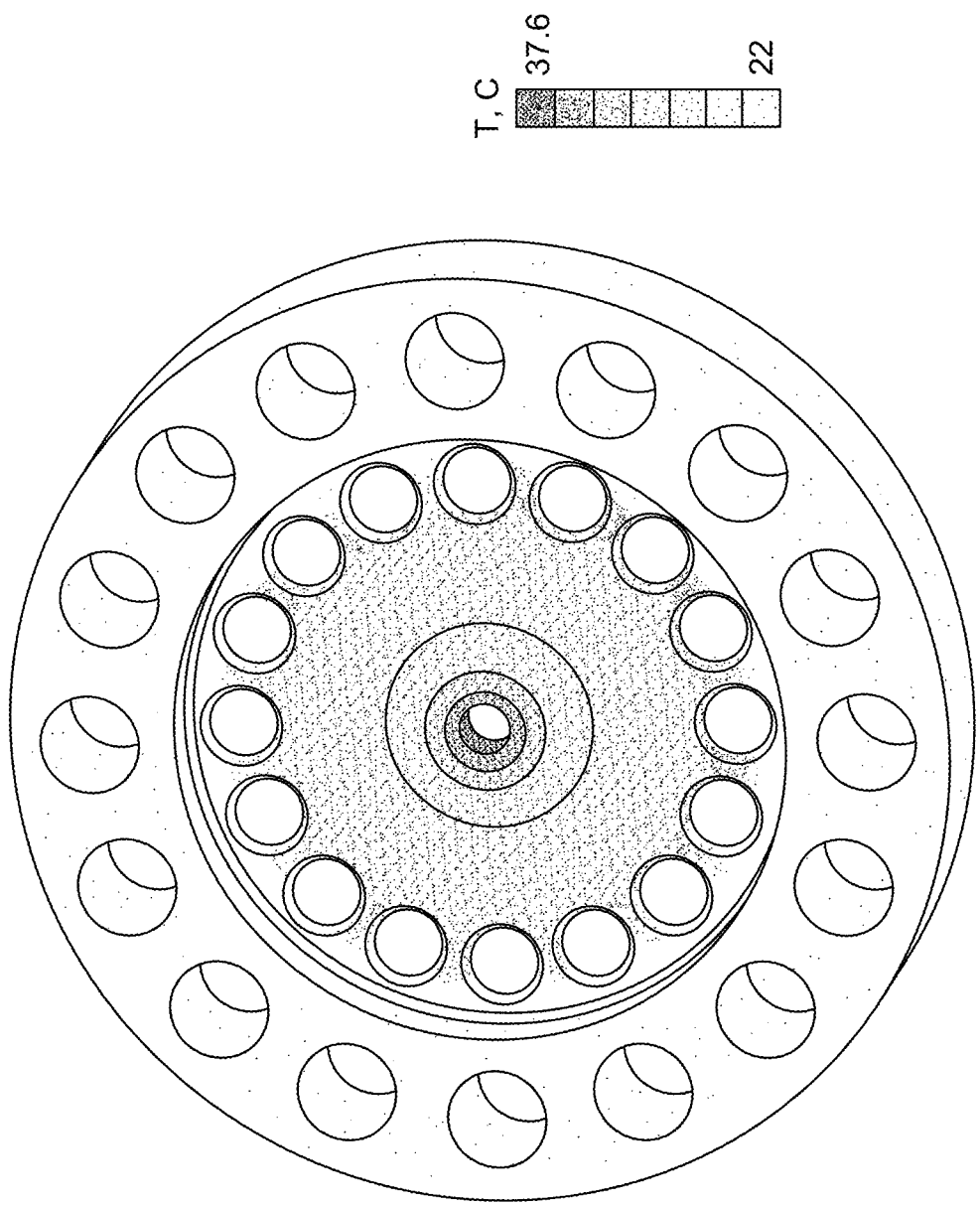
FIG. 15 shows an example temperature map of some high gradient cells.
Figure 16:
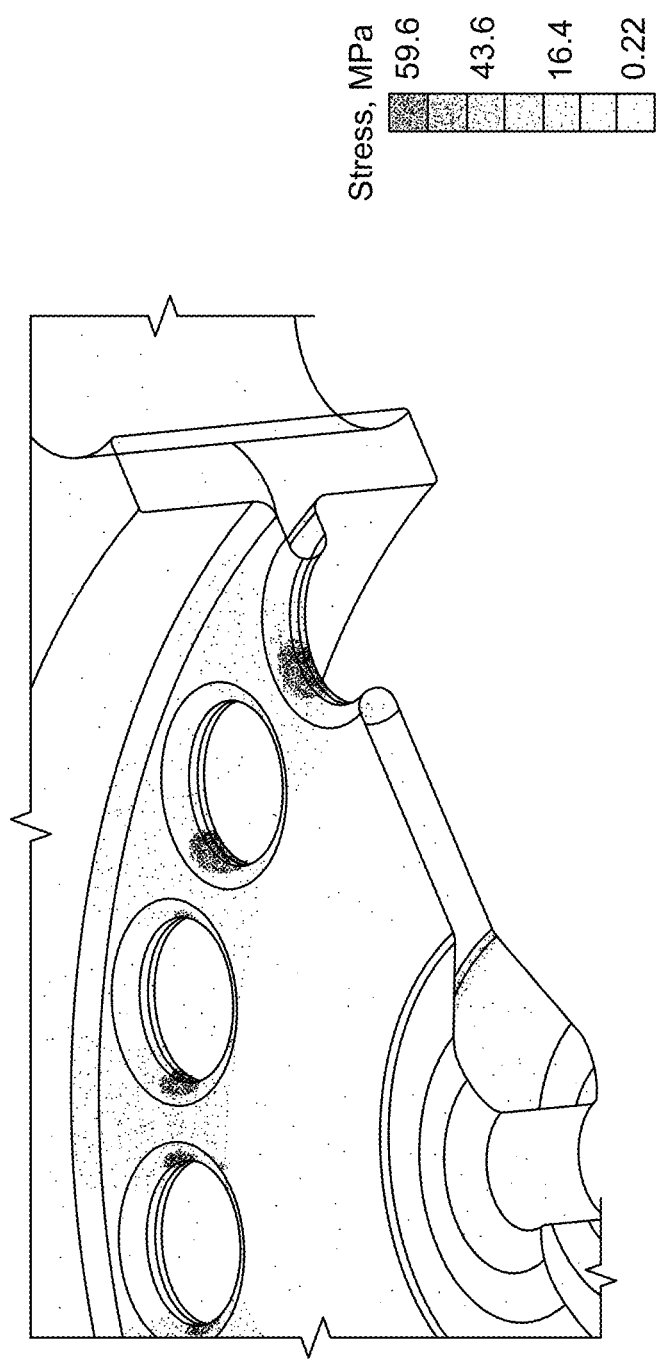
FIG. 16 shows a von Mises stress map of the cells of FIG. 15 under the same conditions.

FIG. 15 shows an example temperature map of some high gradient cells 160. The thermal analysis assumes a pulsed RF regime with 1 μs pulse length and 120 pulses per second repetition rate. Other combinations are possible. As shown, the cells 160 can be configured to maintain a peak temperature below 40° C. FIG. 16 shows a von Mises stress map of the same cells 160 of FIG. 15 under the same conditions. Accordingly, the cells 160 can be configured to maintain a peak stress below 60 MPa.

Conceptual Engineering Design

For certain embodiments, additional steps of the structure design can be taken in the development of the whole accelerating section. A constant gradient structure may be advantageous in maintaining the average 50 MV/m gradient along the structure. The group velocity may be varied along the structure to maintain a constant accelerating gradient. In embodiments having BTW structures, the coupling between cells that defines the group velocity of the structure can be provided by the magnetic field (e.g., via the coupling holes in the iris). This can allow increasing the coupling coefficient while leaving the aperture radius small, and thus not reducing the shunt impedance of the cell.

A method of designing an RF full accelerating section may include designing a constant gradient section, calculating a group velocity modulation, electromagnetic tuning of the accelerating cells, and/or designing input and/or output couplers. FIG. 10 demonstrates an example design of input and output RF power couplers.

Cell Fabrication and Measurements

Test cavity fabrication can be performed through turning and/or milling operations. The axially symmetric cell features such as the nose cones and cell floor and ID/ODs can be performed on a lathe having polycrystalline diamond cutting tools. The coupling, alignment and fastening holes can be completed on a multi-axis (e.g., 3-axis) machining system. End plates may be manufactured with a similar approach.

In some embodiments, the tolerance can be within about +/−10 microns on one or more turned parts. The positional and form requirements on the coupling holes may be within about 100 microns and preferably within about 25 microns of a target requirement.

Example Embodiments

The following provides a list of examples of those described herein. This is a non-exhaustive and non-limiting list of examples.

In a 1st embodiment, a high-gradient accelerating structure configured to accelerate particles, the high gradient accelerating structure comprising: a plurality of accelerating cells, each of the plurality of accelerating cells comprising an iris, the iris of each of the plurality of accelerating cells comprising: an aperture coaxial with a beam axis configured to allow a beam of particles to pass therethrough; and a nose having a maximum thickness greater than an iris thickness; wherein the high gradient accelerating structure is configured to receive the beam of particles along the beam axis at a beam velocity and to propagate electromagnetic waves at a negative first harmonic synchronous with the beam of particles.

In a 2nd embodiment, the high-gradient accelerating structure of example 1, wherein the high-gradient accelerating structure has a total length of less than 45 m.

In a 3rd embodiment, the high-gradient accelerating structure of any of examples 1-2, wherein the high-gradient accelerating structure is configured to apply an energy of at least 200 MeV/u.

In a 4th embodiment, the high-gradient accelerating structure of any of examples 1-3, wherein the high-gradient accelerating structure is configured to accelerate the beam of particles at speeds greater than 0.3 times the speed of light.

In a 5th embodiment, the high-gradient accelerating structure of any of examples 1-4, wherein the high-gradient accelerating structure is configured to accelerate the beam of particles at speeds lower than 0.4 times the speed of light.

In a 6th embodiment, the high-gradient accelerating structure of any of examples 1-5, wherein the high-gradient accelerating structure is configured to produce a gradient of at least 40 MV/m.

In a 7th embodiment, the high-gradient accelerating structure of any of examples 1-6, wherein the high-gradient accelerating structure has a length less than 30 m.

In a 8th embodiment, the high-gradient accelerating structure of any of examples 1-7, wherein the beam of particles comprises particles having a ratio of charge to mass of 0.4 to 1.0.

In a 9th embodiment, the high-gradient accelerating structure of any of examples 1-8, wherein the beam velocity is less than 0.32 times the speed of light.

In a 10th embodiment, the high-gradient accelerating structure of any of examples 1-9, wherein a first radial portion of the nose comprises an increasing thickness radially from the beam axis and a second radial portion comprises a decreasing thickness radially from the beam axis.

In a 11th embodiment, the high-gradient accelerating structure of example 10, wherein a transition between the first radial portion and the second radial portion comprises a smooth surface.

In a 12th embodiment, the high-gradient accelerating structure of any of examples 1-11, wherein a ratio of the maximum thickness of the nose to a thickness of the iris is between 1 and 5.

In a 13th embodiment, the high-gradient accelerating structure of any of examples 1-12, wherein the maximum nose thickness is between 2 and 15 mm.

In a 14th embodiment, the high-gradient accelerating structure of any of examples 1-13, wherein the high-gradient accelerating structure is configured to achieve a shunt impedance of greater than 20 MΩ/m.

In a 15th embodiment, the high-gradient accelerating structure of any of examples 1-14, wherein the high-gradient accelerating structure is configured for operation with a particle source configured to provide a beam having a repetition rate of between 1 Hz and 400 Hz.

In a 16th embodiment, the high-gradient accelerating structure of any of examples 1-15, wherein each of the plurality of irises comprises a plurality of holes spaced from the aperture.

In a 17th embodiment, the high-gradient accelerating structure of example 16, wherein the plurality of holes comprises greater than 4 holes.

In a 18th embodiment, the high-gradient accelerating structure of any of examples 1-17, wherein each of the plurality of holes is disposed at a regular angular interval from a neighboring hole.

In a 19th embodiment, the high-gradient accelerating structure of any of examples 1-18, wherein the particles comprise ions.

In a 20th embodiment, the high-gradient accelerating structure of any of examples 1-19, wherein the particles comprise protons or carbon particles.

In a 21st embodiment, the high-gradient accelerating structure of any of examples 1-20, wherein the nose of each of the plurality of irises is disposed radially about the aperture.

In a 22nd embodiment, a high-gradient accelerating structure configured to accelerate particles, the high gradient accelerating structure comprising: a plurality of high gradient tanks arranged along a beam axis comprising a negative harmonic structure (NHS) tank, the NHS tank comprising: a plurality of accelerating cells, each of the plurality of accelerating cells comprising an iris, the iris of each of the plurality of accelerating cells comprising: an aperture coaxial with the beam axis; and a nose disposed radially about the aperture, the nose having a maximum thickness greater than an iris thickness; wherein the high gradient accelerating structure is configured to propagate electromagnetic waves at a negative harmonic synchronous with particles having a beam velocity greater than 0.3 times the speed of light.

In a 23rd embodiment, the high-gradient accelerating structure of example 22, further comprising a backward traveling wave (BTW) tank configured to receive the beam of particles travelling in a first direction and to propagate a fundamental harmonic of the electromagnetic waves at a second direction opposite the first direction.

In a 24th embodiment, the high-gradient accelerating structure of any of examples 22-23, wherein the high-gradient accelerating structure has a total length of less than 45 m.

In a 25th embodiment, the high-gradient accelerating structure of any of examples 22-24, wherein the negative harmonic comprises a negative first harmonic.

In a 26th embodiment, the high-gradient accelerating structure of any of examples 22-25, wherein the NHS tank is configured to accelerate the beam of particles at greater than 0.35 times the speed of light.

In a 27th embodiment, the high-gradient accelerating structure of any of examples 22-26, wherein the high-gradient accelerating structure is configured to accelerate the beam of particles having a beam pulse width of less than 2 µs.

In a 28th embodiment, the high-gradient accelerating structure of any of examples 22-27, wherein the high-gradient accelerating structure is configured to produce a gradient of at least 30 MV/m.

In a 29th embodiment, the high-gradient accelerating structure of any of examples 22-28, wherein the NHS tank has a length less than 1 m.

In a 30th embodiment, the high-gradient accelerating structure of any of examples 22-29, wherein a first radial portion of the nose comprises an increasing thickness radially from the beam axis and a second radial portion comprises a decreasing thickness radially from the beam axis.

In a 31st embodiment, the high-gradient accelerating structure of any of examples 22-30, wherein a transition between the first radial portion and the second radial portion comprises a smooth surface.

In a 32nd embodiment, the high-gradient accelerating structure of any of examples 22-31, wherein a ratio of the maximum thickness of the nose to a thickness of the iris is between 2 and 5.

In a 33rd embodiment, the high-gradient accelerating structure of any of examples 22-32, wherein the maximum nose thickness is between 4 mm and 11 mm.

In a 34th embodiment, the high-gradient accelerating structure of any of examples 22-33, wherein the high-gradient accelerating structure is configured to achieve a shunt impedance of greater than 30 MΩ/m.

In a 35th embodiment, the high-gradient accelerating structure of any of examples 22-34, wherein the high-gradient accelerating structure is configured for operation with a particle source configured to provide a beam having a repetition rate of between 1 Hz and 400 Hz.

In a 36th embodiment, the high-gradient accelerating structure of any of examples 22-35, wherein each of the plurality of irises comprises a plurality of holes spaced from the aperture.

In a 37th embodiment, the high-gradient accelerating structure of example 36, wherein the plurality of holes comprises greater than 2 holes.

In a 38th embodiment, the high-gradient accelerating structure of any of examples 22-37, wherein each of the plurality of holes is disposed at a regular angular interval from a neighboring hole.

In a 39th embodiment, the high-gradient accelerating structure of any of examples 22-38, wherein the particles comprise hadrons.

In a 40th embodiment, the high-gradient accelerating structure of any of examples 22-39, wherein the particles comprise protons or carbon ions.

In a 41st embodiment, the high-gradient accelerating structure of any of examples 22-40, wherein the nose of each of the plurality of irises is disposed radially about the aperture.

In a 42nd embodiment, the high-gradient accelerating structure of any of examples 22-41, wherein the NHS and BTW tanks of the plurality of tanks have corresponding first and second lengths measured along the beam axis, the first length being shorter than the second length.

In a 43rd embodiment, a linear accelerator comprising: a particle source configured to deliver a beam of particles; a pre-accelerator configured to receive the beam of particles from the particle source and to modify a profile of the beam of particles; and the high-gradient accelerating structure of any of examples 1-42 configured to accelerate the beam of particles.

In a 44th embodiment, the linear accelerator of example 43, wherein the linear accelerator comprises a drift tube linac section and the drift tube is configured to accelerate the beam of particles with an energy of between 3 MeV/u and 20 MeV/u.

In a 45th embodiment, the linear accelerator of any of examples 43-44, wherein the linear accelerator comprises a drift tube linac section and the drift tube is configured to apply an electric field of between 8 MV/m and 10 MV/m.

In a 46th embodiment, the linear accelerator of any of examples 43-45, wherein the linear accelerator comprises a drift tube linac section and the drift tube has a length of between 4 m and 8 m.

In a 47th embodiment, the linear accelerator of any of examples 43-46, wherein the linear accelerator comprises a coupled drift tube linac section and the coupled drift tube is configured to accelerate the beam of particles with an energy of less 45 MeV/u.

In a 48th embodiment, the linear accelerator of any of examples 43-47, wherein the linear accelerator comprises a coupled drift tube linac section and the coupled drift tube is configured to accelerate the beam of particles with an energy of less 45 MeV/u.

In a 49th embodiment, the linear accelerator of any of examples 43-48, wherein the linear accelerator comprises a coupled drift tube linac section and the coupled drift tube is configured to operate on electromagnetic waves having a frequency of between 900 MHz and 1050 MHz.

In a 50th embodiment, the linear accelerator of any of examples 43-49, wherein a total length of the linear accelerator is less than 50 m.

In a 51st embodiment, a cell component for use in a linear particle accelerator, the cell component comprising: a body defining a cell cavity; an iris comprising: a central aperture configured to be disposed about a beam axis; a plurality of holes disposed circumferentially around the aperture; a nose disposed radially between the aperture and the plurality of holes, the nose having a thickness greater than an iris thickness.

In a 52nd embodiment, the cell component of example 51, wherein a first radial portion of the nose comprises an increasing thickness radially from the beam axis and a second radial portion comprises a decreasing thickness radially from the beam axis.

In a 53rd embodiment, the cell component of example 52, wherein a transition between the first radial portion and the second radial portion comprises a smooth surface.

In a 54th embodiment, the cell component of any of examples 52-53, wherein a nose rise angle formed between the beam axis and a flat surface of the second radial portion is between about 50o and 75o.

In a 55th embodiment, the cell component of any of examples 51-54, wherein the plurality of holes comprises a number of holes greater than 3.

In a 56th embodiment, the cell component of any of examples 51-55, wherein each of the plurality of holes is disposed at a regular angular interval from neighboring holes.

In a 57th embodiment, the cell component of any of examples 51-56, wherein a profile of the cell cavity has a circular shape.

In a 58th embodiment, the cell component of any of examples 51-57, wherein the iris has a diameter of between 45 mm and 165 mm.

In a 59th embodiment, the cell component of any of examples 51-58, wherein the aperture has a diameter of between 1.5 mm and 14 mm.

In a 60th embodiment, the cell component of any of examples 51-59, wherein an orbit of the plurality of holes has a radius of between 8 mm and 70 mm.

In a 61st embodiment, the cell component of any of examples 51-60, wherein each of the plurality of holes has a diameter of between 2 mm and 18 mm.

In a 62nd embodiment, the cell component of any of examples 51-61, wherein the body defines a cell length of between 6 mm and 6 cm.

In a 63rd embodiment, the cell component of any of examples 51-62, wherein a ratio of the diameter of each of the holes to the diameter of the aperture is between about 0.75 and 2.5.

In a 64th embodiment, the cell component of any of examples 51-63, wherein a ratio of the diameter of the iris to the length of the cell is between about 1 and 10.

In a 65th embodiment, the cell component of any of examples 51-64, wherein the cell component comprises copper.

In a 66th embodiment, the cell component of any of examples 51-65, wherein the cell component is configured receive a beam of particles along the beam axis and to propagate electromagnetic waves at a negative harmonic synchronous with the beam of particles.

In a 67th embodiment, the cell component of example 66, wherein the negative harmonic comprises a negative first harmonic.

In a 68th embodiment, a method of assembling a linear accelerator, the method comprising: forming a plurality of cells of any of examples 51-67; stacking the plurality of cells; and joining each adjacent cell of the stack.

In a 69th embodiment, the method of example 68, wherein forming a plurality of cells comprises, for each of the plurality of cells, machining the aperture and the plurality of holes from a solid piece of metal.

In a 70th embodiment, the method of any of examples 68-69, wherein stacking the plurality of cells comprises aligning each of the apertures.

In a 71st embodiment, the method of any of examples 68-70, wherein joining each adjacent cell comprises brazing using a copper alloy.

In a 72nd embodiment, the method of any of examples 68-71, wherein joining each adjacent cell comprises welding.

What is claimed is:

1. A high-gradient accelerating structure configured to accelerate particles, the high gradient accelerating structure comprising:
a plurality of accelerating cells, each of the plurality of accelerating cells comprising an iris, the iris of each of the plurality of accelerating cells comprising:
an aperture coaxial with a beam axis configured to allow a beam of particles to pass therethrough; and
a nose having a maximum thickness greater than an iris thickness;
wherein the high gradient accelerating structure is configured to receive the beam of particles along the beam axis at a beam velocity and to propagate electromagnetic waves at a negative first harmonic synchronous with the beam of particles.

2. The high-gradient accelerating structure of claim 1, further comprising a second plurality of accelerating cells coupled to receive the beam of particles from the plurality of accelerating cells and to maintain the electromagnetic waves as a standing wave.

3. The high-gradient accelerating structure of claim 1, wherein the high-gradient accelerating structure has a total length of less than 45 m.

4. The high-gradient accelerating structure of claim 1, wherein the high-gradient accelerating structure is configured to apply an energy of at least 200 MeV/u.

5. The high-gradient accelerating structure of claim 1, wherein the high-gradient accelerating structure is configured to accelerate the beam of particles at speeds greater than 0.3 times the speed of light.

6. The high-gradient accelerating structure of claim 1, wherein the high-gradient accelerating structure is configured to accelerate the beam of particles at speeds lower than 0.4 times the speed of light.

7. The high-gradient accelerating structure of claim 1, wherein the high-gradient accelerating structure is configured to produce a gradient of at least 40 MV/m.

8. The high-gradient accelerating structure of claim 1, wherein the high-gradient accelerating structure has a length less than 30 m.

9. The high-gradient accelerating structure of claim 1, wherein a ratio of the maximum thickness of the nose to a thickness of the iris is between 1 and 5.

10. The high-gradient accelerating structure of claim 1, wherein the high-gradient accelerating structure is configured to achieve a shunt impedance of greater than 20 MΩ/m.

11. A high-gradient accelerating structure configured to accelerate particles, the high gradient accelerating structure comprising:
a plurality of high gradient tanks arranged along a beam axis comprising a negative harmonic structure (NHS) tank, the NHS tank comprising:
a plurality of accelerating cells, each of the plurality of accelerating cells comprising an iris, the iris of each of the plurality of accelerating cells comprising:
an aperture coaxial with the beam axis; and
a nose disposed radially about the aperture, the nose having a maximum thickness greater than an iris thickness;
wherein the high gradient accelerating structure is configured to propagate electromagnetic waves at a negative harmonic synchronous with particles having a beam velocity greater than 0.3 times the speed of light.

12. The high-gradient accelerating structure of claim 11, further comprising a backward traveling wave (BTW) tank configured to receive the beam of particles travelling in a first direction and to propagate a fundamental harmonic of the electromagnetic waves at a second direction opposite the first direction.

13. The high-gradient accelerating structure of claim 11, wherein the NHS tank has a length less than 1 m.

14. The high-gradient accelerating structure of claim 11, wherein the high-gradient accelerating structure is configured to achieve a shunt impedance of greater than 30 MΩ/m.

15. The high-gradient accelerating structure of claim 11, wherein each of the plurality of irises comprises a plurality of holes spaced from the aperture.

16. The high-gradient accelerating structure of claim 12, wherein the NHS and BTW tanks of the plurality of tanks have corresponding first and second lengths measured along the beam axis, the first length being shorter than the second length.

* * * * *